US011046763B2

(12) United States Patent
Weiskopf et al.

(10) Patent No.: US 11,046,763 B2
(45) Date of Patent: *Jun. 29, 2021

(54) TARGETED THERAPY FOR SMALL CELL LUNG CANCER

(71) Applicant: The Board of Trustees of the Leland Stanford Junior University, Stanford, CA (US)

(72) Inventors: Kipp Andrew Weiskopf, Menlo Park, CA (US); Julien Sage, Stanford, CA (US); Irving L. Weissman, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/107,852

(22) PCT Filed: Jan. 8, 2015

(86) PCT No.: PCT/US2015/010650
§ 371 (c)(1),
(2) Date: Jun. 23, 2016

(87) PCT Pub. No.: WO2015/105995
PCT Pub. Date: Jul. 16, 2015

(65) Prior Publication Data
US 2016/0333093 A1    Nov. 17, 2016

Related U.S. Application Data
(60) Provisional application No. 61/925,143, filed on Jan. 8, 2014.

(51) Int. Cl.
| | | |
|---|---|---|
| *C07K 16/28* | (2006.01) | |
| *A61K 38/17* | (2006.01) | |
| *A61K 39/395* | (2006.01) | |
| *A61K 47/68* | (2017.01) | |
| *C07K 16/30* | (2006.01) | |
| *A61K 39/00* | (2006.01) | |

(52) U.S. Cl.
CPC ........ *C07K 16/2803* (2013.01); *A61K 38/177* (2013.01); *A61K 38/1709* (2013.01); *A61K 39/395* (2013.01); *A61K 47/6803* (2017.08); *A61K 47/6857* (2017.08); *A61K 47/6869* (2017.08); *C07K 16/2842* (2013.01); *C07K 16/2896* (2013.01); *C07K 16/3023* (2013.01); *A61K 2039/505* (2013.01); *A61K 2039/507* (2013.01); *C07K 2317/33* (2013.01); *C07K 2317/76* (2013.01)

(58) Field of Classification Search
None
See application file for complete search history.

(56) References Cited

U.S. PATENT DOCUMENTS

| | | |
|---|---|---|
| 9,352,037 B2 | 5/2016 | van den Berg |
| 2004/0213792 A1 | 10/2004 | Clemmons et al. |
| 2010/0028346 A1 | 2/2010 | Lutz et al. |
| 2010/0130587 A1 | 5/2010 | Arber et al. |
| 2010/0166649 A1 | 7/2010 | Shin et al. |
| 2011/0014119 A1* | 1/2011 | Jaiswal .............. C07K 16/3046 424/1.49 |
| 2011/0097345 A1 | 4/2011 | Lambert et al. |
| 2011/0123554 A1* | 5/2011 | Osterroth ......... A61K 47/48276 424/178.1 |
| 2011/0165161 A1 | 7/2011 | Lin et al. |
| 2011/0237498 A1 | 9/2011 | Raymond et al. |
| 2013/0224188 A1 | 8/2013 | Eckelman et al. |

FOREIGN PATENT DOCUMENTS

| | | |
|---|---|---|
| EP | 2 111 869 A1 | 10/2009 |
| JP | 2007-8895 A | 1/2007 |
| JP | 2011-518824 A | 6/2011 |
| JP | 2012-512640 A | 6/2012 |
| JP | 2013-508400 A | 3/2013 |
| WO | 2009/091547 A1 | 7/2007 |
| WO | 2009091547 A1 | 7/2009 |
| WO | 2009091601 A1 | 7/2009 |
| WO | 2010/126452 A1 | 11/2010 |
| WO | 2012/036094 A1 | 3/2012 |

OTHER PUBLICATIONS

Sebastian et al. (Cancer Immunol Immunother, 56: 1637-1644, 2007).*
Zhao et al. (PNAS, 108(45): 18342-18347, 2011).*
Lin et al. (Protein Expression and Purification, 85:109-116, 2012).*
Stancovski et al. (PNAS, 88: 8691-8695, 1991).*
Jiang et al. (J. Biol. Chem., 280: 4656-4662, 2005).*
Majeti et al. (Cell, 138(2): 286-299, 2009).*
Ex parte Peter Gray (Appeal 2017-001821, U.S. Appl. No. 12/615,033).*
Hamilton et al., "Chemotherapy-induced Enrichment of Cancer Stem Cells in Lung Cancer", Journal of Bioanalysis & Biomedicine, Jun. 8, 2013, pp. 1-8, vol. S9:003, OMICS International, Los Angeles, CA.
McKenzie et al., "Identification of a Novel CD56 Lymphokine-activated Killer Cell Precursor in Cancer Patients Receiving Recombinant Interteukin", Cancer Res., Nov. 15, 1992, pp. 6318-6322, vol. 52(22), American Association for Cancer Research, Philadelphia, PA.
Zhan et al., "Development of antibody therapeutics for small cell lung cancer", Expert Opinion on Investigational Drugs, Feb. 2013, pp. 235-244, vol. 22(2), Abstract, PubMed—NCBI, Bethesda MD.

(Continued)

*Primary Examiner* — Nelson B Moseley, II
(74) *Attorney, Agent, or Firm* — Pamela J. Sherwood; Bozicevic, Field & Francis LLP

(57) ABSTRACT

Methods are provided for treatment of lung cancers, particularly small cell lung cancer with targeted therapy, which optionally includes an agent that selectively blocks CD47 binding to SIRPα.

7 Claims, 9 Drawing Sheets
(8 of 9 Drawing Sheet(s) Filed in Color)
Specification includes a Sequence Listing.

(56) References Cited

OTHER PUBLICATIONS

Zheng et al., "Gene expression profiling of CD34+ cells identifies a molecular signature of chronic myeloid leukemia blast crisis", Leukemia, Apr. 13, 2006, pp. 1028-1034, 20, Nature Publishing Group, London, United Kingdom.
Tibes et al., "Activity of Alemtuzumab in Patients with CD52-Positive Acute Leukemia", Cancer, May 10, 2006, pp. 2645-2651, vol. 106, Issue 12, Wiley InterScience, Hoboken, NJ.
Giles, "The Vascular Endothelial Growth Factor (VEGF) Signaling PAthway: A Therapeutic Target in Patients with Hematologic Malignancies", The Oncologist, (2001), pp. 32-39, 1; 6(suppl 5), AlphaMed Press, Durham, NC.
Jaattela, "Multiple cell death pathways as regulators of tumour inititation and progression", Oncogene, (2004) pp. 2746-2756, 23, Nature Publishing Group, London, United Kingdom.
Mawby et al., "Isolation and characterization of CD47 glycoprotein: a multispanning membrane protein which is the same as integrin-associated protein (IAP) and the ovarian tumour marker OA3", Biochem. J., Dec. 1, 1994, pp. 525-530, 304(2), The Biochemical Society, London, United Kingdom.
Karp et al., "Targeting Vascular Endothelial Growth Factor for Relapsed and Refractory Adult Scute Myelogenous Leukemias: Therapy with Sequential 1-fJ-D-Arabinofuranosylcytosine, Mitoxantrone, and Bevacizumab", Clinical Cancer Research, Jun. 1, 2004, pp. 3577-3585, vol. 10, American Association for Cancer Research, Philadelphia, PA.
Oldenborg et al., "CD47-Signal Regulatory Protein a (SIRPa) Regulates Fcy and Complement Receptor-mediated Phagocytosis", J. Exp. Med. Apr. 2, 2001, pp. 855-861, vol. 193 No. 7, The Rockefeller University Press, New York, NY.
Kim et al., "Antibody Engineering for the Development of Therapeutic Antibodies", Molecules and Cells, Aug. 18, 2005, pp. 17-29, vol. 20, No. 1, ResearchGate, Berlin, Germany.
Ozols, "Challenges for chemotherapy in ovarian cancer", Annals of Oncology, May 2006, pp. v181-v187, vol. 17, Suppl 5, European Society for Medical Oncology, Lugano, Switzerland.
Imai et al., "Comparing antibody and small-molecule therapies for cancer", Nature, Sep. 2006, pp. 714-727, vol. 6, Nature Publishing Group, London, United Kingdom.
Alinari et al.,"Alemtuzumab (Campath-1H) in the treatment of chronic lymphocytic leukemia", Oncogene, 2007, pp. 3644-3653, 26, Nature Publishing Group, London, United Kingdom.
Burger et al., "Phase II Trial of Bevacizumab in Persistent or Recurrent Epithelial Ovarian Cancer or Primary Peritoneal Cancer: A Gynecologic Oncology Group Study", Journal of Clinical Oncology, Nov. 20, 2007, pp. 5165-5172, vol. 25, No. 33, American Society of Clinical Oncology, Alexandria, VA.
Clynes et al., "Inhibitory Fc receptors modulate in vivo cytoxicity against tumor targets", Nature Medicine, Apr. 2000, pp. 443-446, vol. 6, No. 4, Nature Publishing Group, London, United Kingdom.
Curriculum Vitae Randolph Wall, Ph.D., 9 pages.
Declaration of Randolph Wall, Ph.D., 107 Pages.
Imai et al., "Comparing antibody and small-molecule therapies for cancer", Nature Reviews/Cancer, Sep. 2006, pp. 714-727, vol. 6, Nature Publishing Group, London, United Kingdom.
Kim et al., "Antibody Engineering for the Development of Therapeutic Antibodies", Molecules and Cells, Aug. 18, 2005, pp. 17-29, vol. 20, No. 1, Korean Society for Molecular and Cellular Biology, Seoul, Korea.
Mawby et al., "Isolation and characterization of CD47 glycoprotein: a multispanning membrane protein which is the same as integrin-associated protein (IAP) and the ovarian tumour marker OA3", Biochem. J., 1994, pp. 525-530, 304, Portland Press Limited, London, United Kingdom.
Musolino et al., Immunoglobulin G Fragment C Receptor Polymorphisms and Clinical Efficacy of Trastuzumab-Based Therapy in Patients With HER-2/neu-Positive Metastatic Breast Cancer, Journal of Clinical Oncology, Apr. 10, 2008, pp. 1789-1796, vol. 26, No. 11, American Society of Clinical Oncology, Alexandria, VA.
Okazawa et al., "Negative Regulation of Phagocytosis in Macrophages by the CD47-SHPS-1 System", The Journal of Immunology, 2005, pp. 2004-2011, 174, The American Association of Immunologists, Inc., Bethesda, MD.
Oldenborg et al., "CD47-Signal Regulatory Protein a (SIRPa) Regulates Fcy and Complement Receptor-mediated Phagocytosis", J. Exp. Med., Apr. 2, 2001, pp. 855-861, vol. 193, No. 7, The Rockefeller University Press, New York, NY.
Ozols, "Challenges for chemotherapy in ovarian cancer", Annals of Oncology, May 2006, pp. v181-v187, vol. 17, Supplement 5, European Society for Medical Oncology, Lugano, Switzerland.
Forty Seven, Inc., Petition for Inter Partes Review of U.S. Pat. No. 9,352,037, Filed: Aug. 5, 2016, Case No. IPR2016-01529, 74 Pages.
Forty Seven, Inc., Petition for Inter Partes Review of U.S. Pat. No. 9,352,037, Filed: Aug. 8, 2016, Case No. IPR2016-01530, 76 Pages.
Tibes et al., "Activity of Alemtuzumab in Patients with CD52-Positive Acute Leukemia", Cancer, Jun. 15, 2006, pp. 2645-2651, vol. 106, No. 12, American Cancer Society, Atlanta, GA.
Veillette et al., "High Expression of Inhibitory Receptor SHPS-1 and Its Association with Protein-tyrosine Phosphatase SHP-1 in Macrophages", The Journal of Biological Chemistry, Aug. 28, 1998, pp. 22719-22728, vol. 273, No. 35, The American Society for Biochemistry and Molecular Biology, Inc., Rockville, MD.
Edris et al., "Antibody therapy targeting the CD47 protein is effective in a model of aggressive metastatic leiomyosarcoma", Proc Natl Acad Sci U S A., Apr. 24, 2012, pp. 6656-6661, vol. 109, No. 17, PNAS, Washington, DC.
Wang et al., "Intravenous delivery of siRNA targeting CD47 effectively inhibits melanoma tumor growth and lung metastasis.", Molecular Therapy: The Journal of the American Society of Gene Therapy, Oct. 10, 2013, pp. 1919-1929, vol. 21, No. 10, ASGCT, Milwaukee, WI.
Maxhimer et al., "Radioprotection in normal tissue and delayed tumor growth by blockade of CD47 signaling", Science Translational Medicine, Oct. 21, 2009, pp. 1-10, vol. 1. No. 3, AAAS, Washington, DC.
Chao et al., "Anti-CD47 antibody synergizes with rituximab to promote phagocytosis and eradicate non-Hodgk in lymphoma", Cell, Sep. 3, 2010, pp. 699-713, vol. 142. No. 5, Elsevier, Amsterdam, Netherlands.
Weiskopf et al., "Engineered SIRP alpha Variants as Immunotherapeutic Adjuvants to Anticancer Antibodies". Science, Jul. 5, 2013, pp. 88-91, vol. 341. No. 6141, AAAS, Washington, DC.
Alblas et al. "Signal regulatory protein alpha ligation induces macrophage nitric oxide production through JAK/STAT-and phosphatidylinositol 3-kinasejRac1/NAPDH oxidase/H202-dependent pathways", Molecular and Cellular Biology, Aug. 2005, pp. 7181-7192, vol. 25. No. 16, American Society for Microbiology, Washington, DC.
Willingham et al., "The CD47-signal regulatory protein alpha (SIRPa) interaction is a therapeutic target for human solid tumors", Proc Natl Acad Sci U S A., Apr. 24, 2012, pp. 6662-6667, vol. 109, No. 17, PNAS, Washington, DC.
Chao et al., "The CD47-SIRPα Pathway in Cancer Immune Evasion and Potential Therapeutic Implications", Curr Opin Immunol., Feb. 4, 2012, pp. 225-232, vol. 24, No. 2, Elsevier, Amsterdam, Netherlands.
Salnikov et al., "Antibody targeting of CD24 efficiently retards growth and influences cytokine milieu in experimental carcinomas", British Journal of Cancer, Mar. 19, 2013, pp. 1449-1459, vol. 108, Springer Nature, Basingstoke, United Kingdom.
Legrand et al (2011) "CD47/signal regulatory protein alpha (SIRPa) interaction is required for optimal human T- and natural killer- (NK) cell homeostasis in vivo", "Proc Natl Acad Sci USA", 108 (32): 13224-1322.
Pietsch et al. (2017) "Anti-leukemic activity and tolerability of anti-human CD47 monoclonal antibodies", Blood Cancer Journal, vol. 7, No. 2, 24, p. e536.

* cited by examiner

Therapeutic targeting of CD47 for small cell lung cancer

CD47-blocking therapies are effective against small cell lung cancer

SEQUENCE LISTING

```
<160> NUMBER OF SEQ ID NOS: 6

<210> SEQ ID NO 1
<211> LENGTH: 5
<212> TYPE: PRT
<213> ORGANISM: Mus musculus

<400> SEQUENCE: 1

Asn Tyr Asn Met His
1               5

<210> SEQ ID NO 2
<211> LENGTH: 17
<212> TYPE: PRT
<213> ORGANISM: Mus musculus

<400> SEQUENCE: 2

Thr Ile Tyr Pro Gly Asn Asp Asp Thr Ser Tyr Asn Gln Lys Phe Lys
1               5                   10                  15

Asp

<210> SEQ ID NO 3
<211> LENGTH: 8
<212> TYPE: PRT
<213> ORGANISM: Mus musculus

<400> SEQUENCE: 3

Gly Gly Tyr Arg Ala Met Asp Tyr
1               5
```

```
<210> SEQ ID NO 4
<211> LENGTH: 16
<212> TYPE: PRT
<213> ORGANISM: Mus musculus

<400> SEQUENCE: 4

Arg Ser Ser Gln Ser Ile Val Tyr Ser Asn Gly Asn Thr Tyr Leu Gly
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Phe Gln Gly Ser His Val Pro Tyr Thr
1               5
```

TARGETED THERAPY FOR SMALL CELL LUNG CANCER

BACKGROUND

Targeted therapies, such as antibodies and specific ligands have proven effective at fighting cancer, especially in cases where conventional therapy fails. Even more encouraging is that antibodies for cancer generally operate in a distinct mechanism from traditional chemotherapy or radiotherapy, so they can often be combined with traditional therapies to generate an additive or synergistic effect.

Antibodies can achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Monoclonal antibodies also bind complement, leading to direct cell toxicity, known as complement dependent cytotoxicity (CDC).

CD47 is a valuable target for anticancer therapy due to its function as an inhibitor of macrophage phagocytosis as well as its broad expression on a variety of human neoplasms. By binding to signal-regulatory protein α (SIRPα), a receptor expressed on the surface of macrophages, CD47 is able to transduce inhibitory signals that prevent phagocytosis. Blocking the interaction between CD47 and SIRPα with antibodies not only stimulates macrophages to engulf cancer cells in vitro but also exerts robust anticancer effects in vivo. Other CD47 blocking agents include "next-generation" CD47 antagonists that bind and block human CD47 with extraordinarily high affinity.

By disabling the inhibitory signals transduced by SIRPα, high-affinity SIRPα variants can reduce the threshold for macrophage activation and promote phagocytic response driven by tumor-specific antibodies. The degree to which the anticancer activity of a given therapeutic antibody is enhanced by CD47 blockade likely depends on multiple factors, including the levels of antigen expression on the surface of malignant cells, the isotype of its heavy chain, and the orientation assumed by the antibody upon antigen binding, which affects its ability to engage Fc receptors on immune effectors. High-affinity SIRPα monomers represent therefore a rapid, safe and effective alternative to several other approaches, including drug/toxin conjugation strategies, that have been pursued in this direction.

Identification of effective targets and combinations of targeted therapies remain of high interest. The present invention addresses this need.

SUMMARY OF THE INVENTION

Methods and compositions are provided for the treatment of lung cancer with a targeted therapy. In some embodiments, the lung cancer is small cell lung cancer. In some embodiments, the therapy is targeted at one or more cell-surface antigens, including CD24, CD166, CD56, CD326, CD298, CD29, CD63, CD9, CD164, CD99, CD46, CD59, CD57, CD165, EpCAM, etc. In some embodiments the targeted therapy comprises administering to an individual suffering from lung cancer a therapeutic dose of an antibody that specifically binds to a cell surface marker selected from CD24, CD166, CD56, CD326, CD298, CD29, CD63, CD9, CD164, CD99, CD46, CD59, CD57, CD165 and EpCAM.

In some embodiments the targeted therapy is combined with a CD47 blocking agent. Cancer cells evade macrophage surveillance by upregulation of CD47 expression. Administration of agents that mask the CD47 protein, e.g. antibodies or small molecules that bind to CD47 or SIRPα and prevent interaction between CD47 and SIRPα, are administered to a patient, which increases the clearance of cancer cells via phagocytosis. The agent that blocks CD47 is combined with monoclonal antibodies directed against one or more lung cancer cell markers, which compositions can be synergistic in enhancing phagocytosis and elimination of cancer cells as compared to the use of single agents.

Specific reagent combinations of interest for therapy include anti-CD47 and anti-CD56; anti-CD47 and anti-CD44, anti-CD47 and anti-CD99, anti-CD47 and anti-Ep-Cam. In some such embodiments the anti-CD47 reagent is a high affinity SIRPα polypeptide, which can be provided in the form of a monomer or a multimer, e.g. as a fusion protein with an IgG Fc polypeptide.

In other embodiments, the therapy provides for a multi-specific antibody that targets CD47 and a second cancer cell marker, including multispecific antibodies that target CD47 and CD56; CD47 and CD44, CD47 and EpCam, etc. Compositions of such multispecific antibodies are also provided, where the multispecific antibody is desirably human or humanized; and may be modified to extend the blood half-life, e.g. by pegylation, etc.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Figure 1:
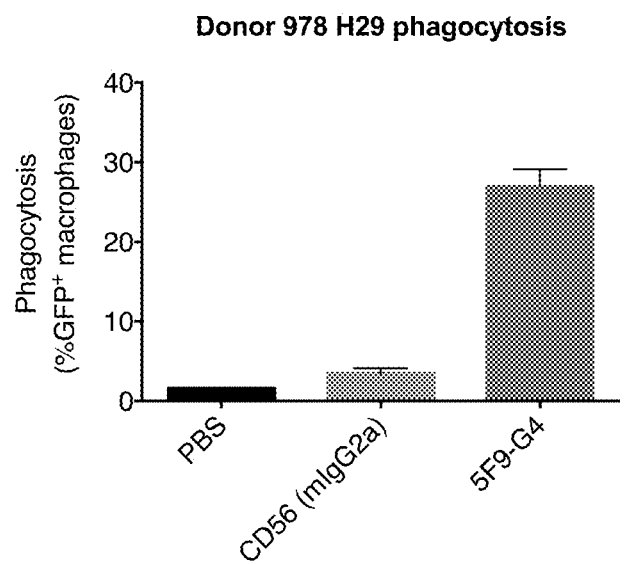
FIG. 1: CD47-blocking therapies stimulate macrophage phagocytosis of small cell lung cancer. Human monocytes from anonymous blood donors were purified by magnetic activated cell sorting (MACS) using CD14+ selection. Monocytes were cultured in the presence of 10% AB human serum for one week, at which point the exhibited morphological changes characteristic of differentiation to macrophages. Macrophages were co-cultured with primary human small cell lung cancer cells (SCLC sample "H29") labeled with a green fluorescent dye. Cells were treated with either a vehicle control (phosphate buffered saling, PBS), anti-CD56 antibody (clone MEM-188), or humanized anti-CD47 antibody (clone 5F9-G4). Phagocytosis was evaluated by high-throughput flow cytometry as the percentage of macrophages that had engulfed green fluorescent SCLC cells. Treatment with anti-CD47 antibody was able to induce elevated levels of phagocytosis as a single agent.
Figure 2:
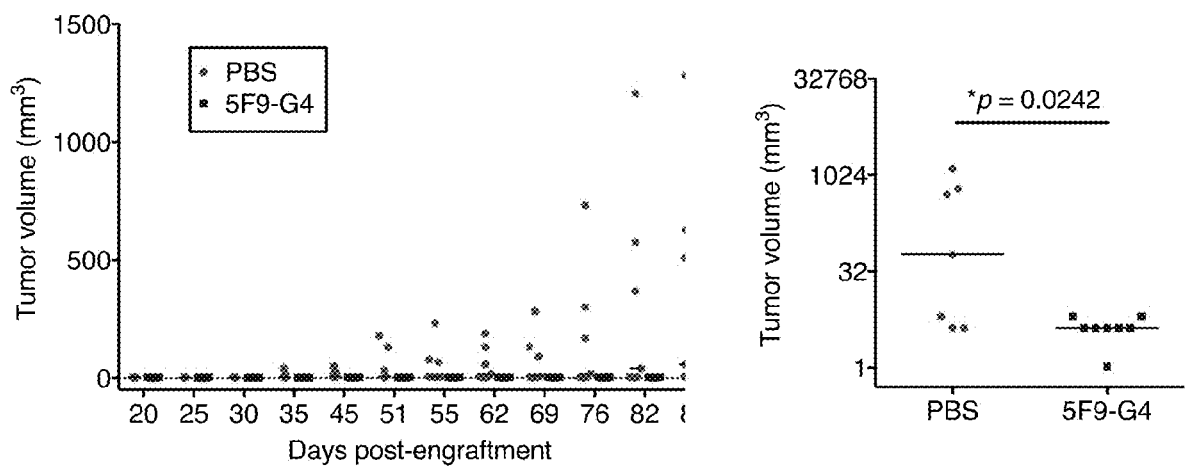
FIG. 2: CD47-blockade produces a therapeutic response against small cell lung cancer cells in vivo using mouse xenotransplantation models. Primary small cell lung cancer cells (sample H29) were engrafted into immunodeficient NSG mice. After approximately three weeks of growth, mice were randomized into two treatment cohorts. The first cohort was treated with a vehicle control (phosphate buffered saline, PBS; red), and the second cohort was treated with daily injections of 250 μg anti-CD47 antibody (clone 5F9-G4, blue). Tumor growth was monitored over time. Each point represents a tumor growing in an individual mouse. Black bars represent median tumor volume. Left Tumor volume measurements over entire time course of study. Right Tumor volume measurements on day 89 of study. Note logarithmic scale.
Figure 3:
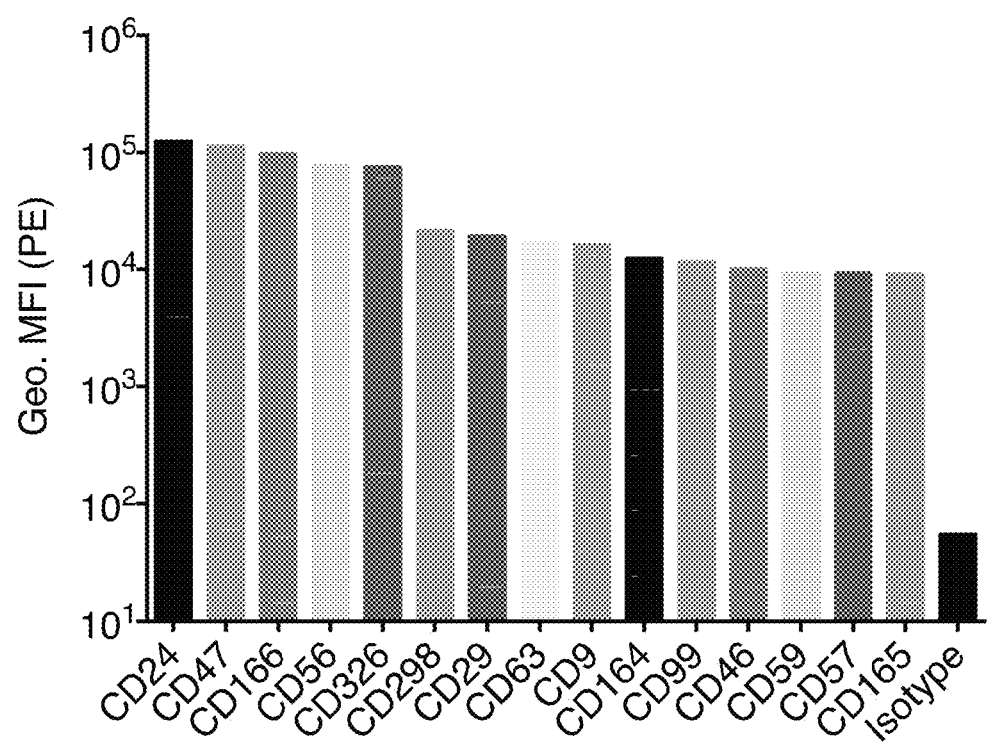
FIG. 3: Novel therapeutic targets highly expressed on the surface of small cell lung cancer cells. Primary human small cell lung cancer cells (sample H29) were subjected to comprehensive flow cytometric immunophenotyping using a LEGENDScreen assay (Biolegend). Surface antigens were ranked based on their geometric mean fluorescence intensity (Geo. MFI). These antigens are therapeutic targets for antibodies in combination with CD47-blocking agents.
Figure 4:
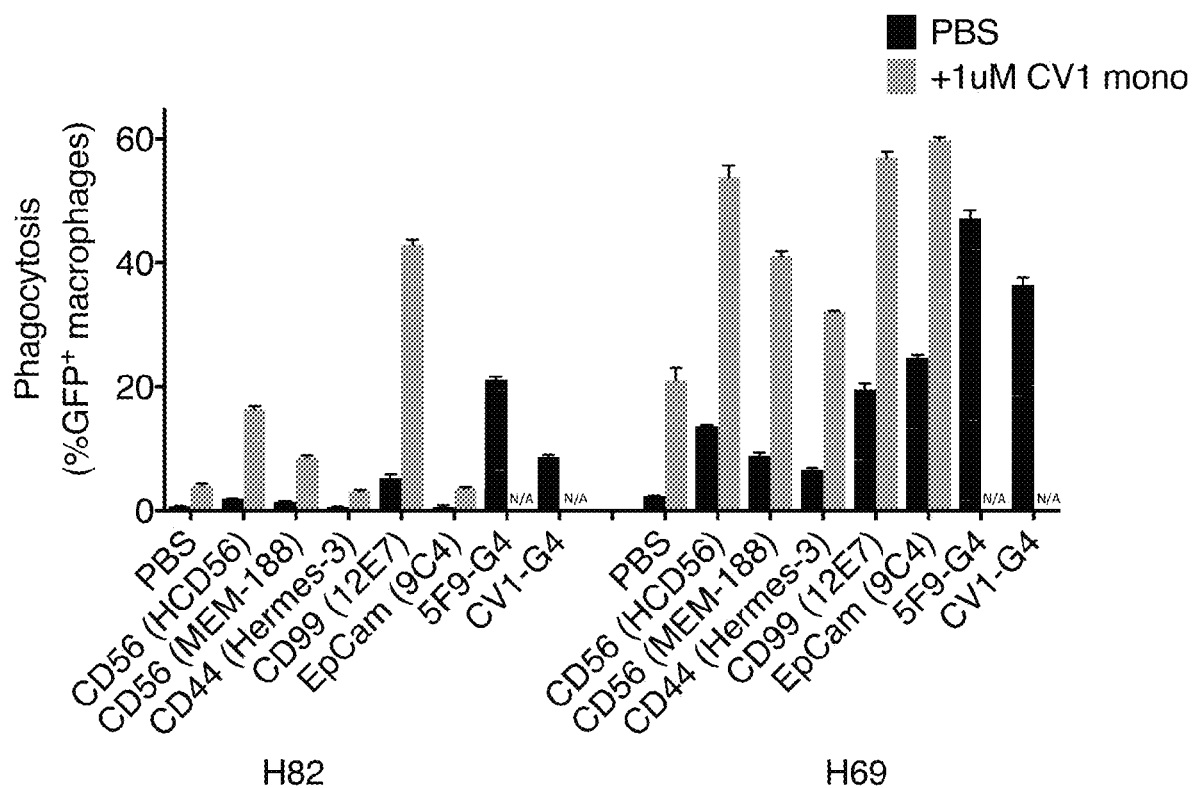
FIG. 4: The ability of SCLC-targeting antibodies to induce macrophage phagocytosis can be enhanced by combination with CD47-blocking therapies. Two human small cell lung cancer cell lines (H82 and H69) were labeled with a green fluorescent dye, and then were co-cultured with primary NSG mouse macrophages in the presence of the indicated antibodies either in combination with vehicle control (phosphate buffered saline, PBS; gray) or with high-affinity SIRPalpha variant CV1 monomer (black). Phagocytosis was evaluated by high-throughput flow cytometry as the percentage of macrophages that had engulfed green fluorescent SCLC cells. Anti-CD47 reagents 5F9-G4 and CV1-G4 were not tested in combination with CV1 monomer due to direct competition.

Methods and compositions are provided for the treatment of lung cancer with a therapeutic agent, e.g. an antibody, targeted to a marker of lung cancer, e.g. targeted to one or more cell-surface antigens, including CD24, CD166, CD56, CD326, CD298, CD29, CD63, CD9, CD164, CD99, CD46, CD59, CD57, CD165, EpCAM, etc. In some embodiments, a combination, e.g. a synergistic combination, of agents is provided, wherein one agent is an anti-CD47 blocking agent, and the second agent is targeted to a lung cancer marker, e.g. CD24, CD166, CD56, CD326, CD298, CD29, CD63, CD9, CD164, CD99, CD46, CD59, CD57, CD165, EpCAM, etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Synergistic combination. Synergistic combinations may provide for a therapeutic effect that is comparable to the effectiveness of a monotherapy, i.e. the individual components of the combination, while reducing adverse side effects, e.g. damage to non-targeted tissues, immune status, and other clinical indicia. Alternatively synergistic combinations may provide for an improved effectiveness when compared to the effectiveness of a monotherapy, i.e. the individual components of the combination, which effect may be measured by total tumor cell number; length of time to relapse; and other indicia of patient health.

Synergistic combinations of the present invention combine an agent that is targeted to inhibit or block CD47 function; and an agent that is targeted to inhibit or block a second lung cancer cell marker, usually a cell surface marker. The combination may be provided with a combination of agents, e.g. two distinct proteins, each of which is specific for a different marker; or may be provided as a multispecific agent, e.g. antibody, that combines specificity for two or more different markers.

Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Dosage Form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing Regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

CD47 polypeptides. The three transcript variants of human CD 47 (variant 1, NM 001777; variant 2, NM 198793; and variant 3, NM 001025079) encode three isoforms of CD47 polypeptide. CD47 isoform 1 (NP 001768), the longest of the three isoforms, is 323 amino acids long. CD47 isoform 2 (NP 942088) is 305 amino acid long. CD47 isoform 3 is 312 amino acids long. The three isoforms are identical in sequence in the first 303 amino acids. Amino acids 1-8 comprise the signal sequence, amino acids 9-142 comprise the CD47 immunoglobulin like domain, which is the soluble fragment, and amino acids 143-300 is the transmembrane domain.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. Derivatives and fusion of soluble CD47 find use as CD47 mimetic molecules.

The first 142 amino acids of CD47 polypeptide comprise the extracellular region of CD47. The three isoforms have identical amino acid sequence in the extracellular region, and thus any of the isoforms are can be used to generate soluble CD47. "Soluble CD47" is a CD47 protein that lacks the transmembrane domain. Soluble CD47 is secreted out of the cell expressing it instead of being localized at the cell surface.

In vitro assays for CD47 biological activity include, e.g. inhibition of phagocytosis of porcine cells by human macrophages, binding to SIRP α receptor, SIRP α tyrosine phosphorylation, etc. An exemplary assay for CD47 biological activity contacts a human macrophage composition in the presence of a candidate agent. The cells are incubated with the candidate agent for about 30 minutes and lysed. The cell lysate is mixed with anti-human SIRP α antibodies to immunoprecipitate SIRPα. Precipitated proteins are resolved by SDS PAGE, then transferred to nitrocellulose and probed with antibodies specific for phosphotyrosine. A candidate agent useful as a CD47 mimetic increases SIRPα tyrosine phosphorylation by at least 10%, or up to 20%, or 50%, or 70% or 80% or up to about 90% compared to the level of phosphorylation observed in the absence of candidate agent. Another exemplary assay for CD47 biological activity measures phagocytosis of hematopoietic cells by human macrophages. A candidate agent useful as a CD47 mimetic results in the down regulation of phagocytosis by at least about 10%, at least about 20%, at least about 50%, at least about 70%, at least about 80%, or up to about 90% compared to level of phagocytosis observed in absence of candidate agent.

By "manipulating phagocytosis" is meant an up-regulation or a down-regulation in phagocytosis by at least about 10%, or up to 20%, or 50%, or 70% or 80% or up to about 90% compared to level of phagocytosis observed in absence of intervention. Thus in the context of decreasing phagocytosis of circulating hematopoietic cells, particularly in a transplantation context, manipulating phagocytosis means a down-regulation in phagocytosis by at least about 10%, or up to 20%, or 50%, or 70% or 80% or up to about 90% compared to level of phagocytosis observed in absence of intervention.

Anti-CD47 agent. As used herein, the term "anti-CD47 agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα. In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell).

The efficacy of a suitable anti-CD47 agent can be assessed by assaying the agent (further described below). In an exemplary assay, target cells are incubated in the presence or absence of the candidate agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell by apoptosis.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity.

A SIRPα reagent can be used as a "monomer", in which the binding domain of SIRPα is used, but where the binding domain is provided as a soluble monomeric protein. In other embodiments, a SIRPα variant of the present invention is a fusion protein, e.g., fused in frame with a second polypeptide, particularly where the second polypeptide provides for multimerization. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding, for example an antibody that does not induce apoptosis upon binding. Non-limiting examples of suitable antibodies include clones B6H12, 5F9, 8B6, and C3 (for example as described in International Patent Publication WO 2011/143624, herein specifically incorporated by reference). The 5F9 antibody comprises CDR sequences (SEQ ID NO:1) 5F9 heavy chain CDR1: NYNMH; (SEQ ID NO:2) 5F9 heavy chain CDR2: TIYPGNDDTSYNQKFKD; (SEQ ID NO:3) 5F9 heavy chain CDR3: GGYRAMDY; (SEQ ID NO:4) 5F9 light chain CDR1: RSSQSIVYSNG-NTYLG; (SEQ ID NO:5) 5F9 light chain CDR2: KVSNRFS; (SEQ ID NO:6) 5F9 light chain CDR3: FQGSHVPYT. Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length.

The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to a reference human CD47 sequence.

The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH. Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. In addition, the antibodies or antigen binding fragments may be produced by genetic engineering. Humanized, chimeric, or xenogeneic human antibodies, which produce less of an immune response when administered to humans, are preferred for use in the present invention.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ricin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Antibodies include free antibodies and antigen binding fragments derived therefrom, and conjugates, e.g. pegylated antibodies, drug, radioisotope, or toxin conjugates, and the like. Monoclonal antibodies directed against a specific epitope, or combination of epitopes, will allow for the targeting and/or depletion of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

Humanized versions of such antibodies are also within the scope of this invention. Humanized antibodies are especially useful for in vivo applications in humans due to their low antigenicity.

The phrase "multispecific or bispecific antibody" refers to a synthetic or recombinant antibody that recognizes more than one protein. Bispecific antibodies directed against a combination of epitopes, will allow for the targeting and/or depletion of cellular populations expressing the combination of epitopes. Exemplary bi-specific antibodies include those targeting a combination of CD47 and an SCLC cancer cell marker. Generation of bi-specific antibodies are described in the literature, for example, in U.S. Pat. Nos. 5,989,830, 5,798,229, which are incorporated herein by reference. Higher order specificities, e.g. trispecific antibodies, are described by Holliger and Hudson (2005) Nature Biotechnology 23:1126-1136.

The efficacy of a CD47 inhibitor can be assessed by assaying CD47 activity. The above-mentioned assays or modified versions thereof are used. In an exemplary assay, SCLC are incubated with bone marrow derived macrophages, in the presence or absence of the candidate agent. An inhibitor of the cell surface CD47 will up-regulate phagocytosis by at least about 10%, or up to 20%, or 50%, or 70% or 80% or up to about 90% compared to the phagocytosis in absence of the candidate agent. Similarly, an in vitro assay for levels of tyrosine phosphorylation of SIRPα will show a decrease in phosphorylation by at least about 10%, or up to 20%, or 50%, or 70% or 80% or up to about 90% compared to phosphorylation observed in absence of the candidate agent.

In one embodiment of the invention, the agent, or a pharmaceutical composition comprising the agent, is provided in an amount effective to detectably inhibit the binding of CD47 to SIRPα receptor present on the surface of phagocytic cells. The effective amount is determined via empirical testing routine in the art. The effective amount may vary depending on the number of cells being transplanted, site of transplantation and factors specific to the transplant recipient.

The terms "phagocytic cells" and "phagocytes" are used interchangeably herein to refer to a cell that is capable of phagocytosis. There are four main categories of phagocytes: macrophages, mononuclear cells (histiocytes and monocytes); polymorphonuclear leukocytes (neutrophils) and dendritic cells.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, e.g. mouse, rat, rabbit, pig, primate, including humans and other apes, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "recipient", "individual", "subject", "host", and "patient", used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" refers to a gene or gene product that, upon modulation of its activity (e.g., by modulation of expression, biological activity, and the like), can provide for modulation of the cancerous phenotype. As used throughout, "modulation" is meant to refer to an increase or a decrease in the indicated phenomenon (e.g., modulation of a biological activity refers to an increase in a biological activity or a decrease in a biological activity).

Lung Cancer

Lung carcinoma is the leading cause of cancer-related death worldwide. About 85% of cases are related to cigarette smoking. Symptoms can include cough, chest discomfort or pain, weight loss, and, less commonly, hemoptysis; however, many patients present with metastatic disease without any clinical symptoms. The diagnosis is typically made by chest x-ray or CT and confirmed by biopsy. Depending on the stage of the disease, treatment includes surgery, chemotherapy, radiation therapy, or a combination. For the past several decades, the prognosis for a lung cancer patient has been poor, particularly for patients with stage IV (metastatic) disease.

Respiratory epithelial cells require prolonged exposure to cancer-promoting agents and accumulation of multiple genetic mutations before becoming neoplastic (an effect called field carcinogenesis). In some patients with lung cancer, secondary or additional mutations in genes that stimulate cell growth (K-ras, MYC), cause abnormalities in growth factor receptor signaling (EGFR, HER2/neu), and inhibit apoptosis contribute to proliferation of abnormal cells. In addition, mutations that inhibit tumor-suppressor genes (p53, APC) can lead to cancer. Other mutations that may be responsible include the EML-4-ALK translocation and mutations in ROS-1, BRAF, and PI3KCA. Genes such as these that are primarily responsible for lung cancer are called driver mutations. Although driver mutations can cause or contribute to lung cancer among smokers, these mutations are particularly likely to be a cause of lung cancer among nonsmokers.

Chest x-ray is often the initial imaging test. It may show clearly defined abnormalities, such as a single mass or multifocal masses or a solitary pulmonary nodule, an enlarged hilum, widened mediastinum, tracheobronchial narrowing, atelectasis, non-resolving parenchymal infiltrates, cavitary lesions, or unexplained pleural thickening or effusion. These findings are suggestive but not diagnostic of lung cancer and require follow-up with CT scans or combined PET-CT scans and cytopathologic confirmation.

CT shows many characteristic anatomic patterns and appearances that may strongly suggest the diagnosis. CT also can guide core needle biopsy of accessible lesions and is useful for staging. If a lesion found on a plain x-ray is highly likely to be lung cancer, PET-CT may be done. This study combines anatomic imaging from CT with functional imaging from PET. The PET images can help differentiate inflammatory and malignant processes.

SCLC has 2 stages: limited and extensive. Limited-stage SCLC disease is cancer confined to one hemithorax (including ipsilateral lymph nodes) that can be encompassed within one tolerable radiation therapy port, unless there is a pleural or pericardial effusion. Extensive-stage disease is cancer outside a single hemithorax or the presence of malignant cells detected in pleural or pericardial effusions. Less than one third of patients with SCLC will present with limited-stage disease; the remainder of patients often have extensive distant metastases. The overall prognosis for SCLC is poor. The median survival time for limited-stage SCLC is 20 mo, with a 5-yr survival rate of 20%. Patients with extensive-stage SCLC do especially poorly, with a 5-yr survival rate of <1%.

NSCLC has 4 stages, I through IV (using the TNM system). TNM staging is based on tumor size, tumor and lymph node location, and the presence or absence of distant metastases. The 5-yr survival rate of patients with NSCLC varies by stage, from 60 to 70% for patients with stage I disease to <1% for patients with stage IV disease.

Conventional treatment varies by cell type and by stage of disease. Many patient factors not related to the tumor affect treatment choice. Poor cardiopulmonary reserve, undernutrition, frailty or poor physical performance status, comorbidities, including cytopenias, and psychiatric or cognitive illness all may lead to a decision for palliative over curative treatment or for no treatment at all, even though a cure with aggressive therapy might technically be possible.

SCLC of any stage is typically initially responsive to treatment, but responses are usually short-lived. Chemotherapy, with or without radiation therapy, is given depending on the stage of disease. In many patients, chemotherapy prolongs survival and improves quality of life enough to warrant its use. Surgery generally plays no role in treatment of SCLC, although it may be curative in the rare patient who has a small focal tumor without spread (such as a solitary pulmonary nodule) who underwent surgical resection before the tumor was identified as SCLC. Chemotherapy regimens of etoposide and a platinum compound (either cisplatin or carboplatin) are commonly used, as are other drugs, such as irinotecan, topotecan, vinca alkaloids (vinblastine, vincristine, vinorelbine), alkylating agents (cyclophosphamide, ifosfamide), doxorubicin, taxanes (docetaxel, paclitaxel), and gemcitabine. When disease is confined to a hemithorax, radiation therapy further improves clinical outcomes; such response to radiation therapy was the basis for the definition of limited-stage disease. The use of cranial radiation to prevent brain metastases is also advocated in certain cases; micrometastases are common in SCLC, and chemotherapy has less ability to cross the blood-brain barrier.

In extensive-stage disease, treatment is based on chemotherapy rather than radiation therapy, although radiation therapy is often used as palliative treatment for metastases to bone or brain. In patients with an excellent response to chemotherapy, prophylactic brain irradiation is sometimes used as in limited-stage SCLC to prevent growth of SCLC in the brain.

Treatment for NSCLC typically involves assessment of eligibility for surgery followed by choice of surgery, chemotherapy, radiation therapy, or a combination of modalities as appropriate, depending on tumor type and stage.

Treatment of Cancer

The invention provides methods for reducing growth of lung cancer cells through the introduction of an effective dose of a targeted therapeutic agent directed to a lung cancer cell surface marker, including without limitation CD24, CD166, CD56, CD326, CD298, CD29, CD63, CD9, CD164, CD99, CD46, CD59, CD57, CD165, EpCAM, etc. In some embodiments the marker is one of CD56, CD44, CD99 and EpCam. In preferred embodiments the targeted therapeutic agent is combined with a CD47 blocking agent, e.g. soluble SIRPα monomer or multimer, an anti-CD47 antibody, small molecule, etc. In certain embodiments the cancer is SCLC. By blocking the activity of CD47, the downregulation of phagocytosis that is found with certain tumor cells is prevented.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with SCLC, etc.

Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

As an alternative embodiment, an agent, e.g. a chemotherapeutic drug that reduces cancer cell growth, can be targeted to a cancer cell by conjugation to a CD47 specific antibody. Thus, in some embodiments, the invention provides a method of delivering a drug to a cancer cell, comprising administering a drug-antibody complex to a subject, wherein the antibody is specific for a cancer-associated polypeptide, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

In certain embodiments, a bi-specific antibody may be used. For example a bi-specific antibody in which one antigen binding domain is directed against CD47 and the other antigen binding domain is directed against a cancer cell marker, such as CD24, CD166, CD56, CD326, CD298, CD29, CD63, CD9, CD164, CD99, CD46, CD59, CD57, CD165, EpCAM, etc. may be used.

Generally, as the term is utilized in the specification, "antibody" or "antibody moiety" is intended to include any polypeptide chain-containing molecular structure that has a specific shape which fits to and recognizes an epitope, where one or more non-covalent binding interactions stabilize the complex between the molecular structure and the epitope. For monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Antibodies which have a reduced propensity to induce a violent or detrimental immune response in humans (such as anaphylactic shock), and which also exhibit a reduced propensity for priming an immune response which would prevent repeated dosage with the antibody therapeutic or imaging agent (e.g., the human-anti-murine-antibody "HAMA" response), are preferred for use in the invention. These antibodies are preferred for all administrative routes. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals which have been genetically altered to produce human immunoglobulins. The transgenic animal may be produced by initially producing a "knockout" animal which does not produce the animal's natural antibodies, and stably transforming the animal with a human antibody locus (e.g., by the use of a human artificial chromosome). Only human antibodies are then made by the animal. Techniques for generating such animals, and deriving antibodies therefrom, are described in U.S. Pat. Nos. 6,162,963 and 6,150,584, incorporated fully herein by reference. Such fully human xenogenic antibodies are a preferred antibody for use in the methods and compositions of the present invention. Alternatively, single chain antibodies can be produced from phage libraries containing human variable regions. See U.S. Pat. No. 6,174,708, incorporated fully herein by reference.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879 5883 (1988) and Bird et al., Science 242:423 426 (1988), both fully incorporated herein, by reference. These are single chain Fvs which have been found to retain specificity and affinity and have been shown to be useful for imaging tumors and to make recombinant immunotoxins for tumor therapy. However, researchers have found that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

Derivatized polypeptides with added chemical linkers, detectable moieties such as fluorescent dyes, enzymes, substrates, chemiluminescent moieties, specific binding moieties such as streptavidin, avidin, or biotin, or drug conjugates may be utilized in the methods and compositions of the present invention.

In some embodiments of the invention, the polypeptide reagents of the invention are coupled or conjugated to one or more therapeutic, cytotoxic, or imaging moieties. As used herein, "cytotoxic moiety" (C) simply means a moiety which inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. Agents may be conjugated to a polypeptide reagent of the invention by any suitable technique, with appropriate consideration of the need for pharmokinetic stability and reduced overall toxicity to the patient. A therapeutic agent may be coupled to a suitable moiety either directly or indirectly (e.g. via a linker group). A direct reaction is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance a polypeptide reagent of the invention from an agent in order to avoid interference with binding capabilities. A linker group can also serve to increase the chemical reactivity of a substituent on a moiety or a polypeptide reagent of the invention, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic moieties may be coupled to a polypeptide reagent of the invention through a an oxidized carbohydrate group at a glycosylation site, as described in U.S. Pat. Nos. 5,057,313 and 5,156,840. Yet another alternative method of coupling a polypeptide reagent of the invention to a cytotoxic or therapeutic moiety is by the use of a non-covalent binding pair, such as streptavidin/biotin, or avidin/biotin. In these embodiments, one member of the pair is covalently coupled to the anti-CD47, CV1, etc. moiety and the other member of the binding pair is covalently coupled to the therapeutic, cytotoxic, or imaging moiety.

Where a cytotoxic moiety is more potent when free from the binding portion of a polypeptide reagent of the invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one moiety to a polypeptide reagent of the invention. By poly-derivatizing the reagent, several strategies may be simultaneously implemented, e.g. a therapeutic antibody may be labeled for tracking by a visualization technique. Regardless of the particular embodiment, conjugates with more than one moiety may be prepared in a variety of ways. For example, more than one moiety may be coupled directly to a polypeptide molecule, or linkers which provide multiple sites for attachment (e.g., dendrimers) can be used. Alternatively, a carrier with the capacity to hold more than one cytotoxic or imaging moiety can be used.

A carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful for imaging moiety conjugation to antibody moieties for use in the invention, as a sufficient amount of the imaging moiety (dye, magnetic resonance contrast reagent, etc.) for detection may be more easily associated with the antibody moiety. In addition, encapsulation carriers are also useful in chemotoxic therapeutic embodiments, as they can allow the therapeutic compositions to gradually release a chemotoxic moiety over time while concentrating it in the vicinity of the tumor cells.

Preferred radionuclides for use as cytotoxic moieties are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use.

Preferred chemotoxic agents include small-molecule drugs such as carboplatin, cisplatin, vincristine, taxanes such as paclitaxel and docetaxel, hydroxyurea, gemcitabine, vinorelbine, irinotecan, tirapazamine, matrilysin, methotrexate, pyrimidine and purine analogs, and other suitable small toxins known in the art. Preferred chemotoxin differentiation inducers include phorbol esters and butyric acid. Chemotoxic moieties may be directly conjugated to the antibody moiety via a chemical linker, or may be encapsulated in a carrier, which is in turn coupled to the antibody. Preferred toxin proteins for use as cytotoxic moieties include ricins A and B, abrin, diphtheria toxin, bryodin 1 and 2, momordin, trichokirin, cholera toxin, gelonin, *Pseudomonas* exotoxin, *Shigella* toxin, pokeweed antiviral protein, and other toxin proteins known in the medicinal biochemistry arts. As these toxin agents may elicit undesirable immune responses in the patient, especially if injected intravascularly, it is preferred that they be encapsulated in a carrier for coupling to the antibody.

For administration, a targeted therapeutic agent, or combination of targeted therapeutic agents may be administered separately or together; and will generally be administered within the same general time frame, e.g. within a week, within 3-4 days, within 1 day or simultaneously with each other.

The agent or agents are mixed, prior to administration, with a non-toxic, pharmaceutically acceptable carrier substance. Usually, this will be an aqueous solution, such as normal saline or phosphate-buffered saline (PBS), Ringers solution, lactate-Ringers solution, or any isotonic physiologically acceptable solution for administration by the chosen means. Preferably, the solution is sterile and pyrogen-free, and is manufactured and packaged under current Good Manufacturing Processes (GMPs), as approved by the FDA. The clinician of ordinary skill is familiar with appropriate ranges for pH, tonicity, and additives or preservatives when formulating pharmaceutical compositions for administration by intravascular injection, direct injection into the lymph nodes, intraperitoneal, or by other routes. In addition to additives for adjusting pH or tonicity, the agents may be stabilized against aggregation and polymerization with amino acids and non-ionic detergents, polysorbate, and polyethylene glycol. Optionally, additional stabilizers may include various physiologically-acceptable carbohydrates and salts. Also, polyvinylpyrrolidone may be added in addition to the amino acid. Suitable therapeutic immunoglobulin solutions which are stabilized for storage and administration to humans are described in U.S. Pat. No. 5,945,098, incorporated fully herein by reference. Other agents, such as human serum albumin (HSA), may be added to the therapeutic or imaging composition to stabilize the antibody conjugates.

The compositions of the invention may be administered using any medically appropriate procedure, e.g., intravascular (intravenous, intraarterial, intracapillary) administration, injection into the tumor, etc. Intravascular injection may be by intravenous or intraarterial injection. The effective amount of the therapeutic compositions to be given to a particular patient will depend on a variety of factors, several of which will be different from patient to patient. A competent clinician will be able to determine an effective amount of a therapeutic composition to administer to a patient to retard the growth and promote the death of tumor cells. Dosage of the agents will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an locally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic or imaging composition in the course of routine clinical trials.

Typically an effective dosage will be 0.001 to 100 milligrams of antibody per kilogram subject body weight. The ratio of anti-CD47 to the second agent may range from 1:100; 1:50; 1:10; 1:5; 1:2; 1:1; 2:1; 5:1; 10:1; 50:1; 100:1. The agents can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, antibody moieties which do not provoke HAMA or other immune responses are preferred.

Example 1

High-Affinity SIRPα Variants Enhance Macrophage Destruction of Small Cell Lung Cancer CD47 allows cancer cells to evade the immune system by signaling through SIRPα, an inhibitory receptor on macrophages. We recently developed next-generation CD47 antagonists by engineering the N-terminal immunoglobulin domain of SIRPα. These "high-affinity SIRPα variants" have an affinity for human CD47 ($K_D$) as low as 11.1 pM, approximately 50,000-fold improved over wild-type SIRPα. When combined with tumor-specific antibodies, the high-affinity SIRPα variants act as immunotherapeutic adjuvants to maximize macrophage destruction of cancer cells.

We have now applied these reagents to small cell lung cancer (SCLC), a cancer with poor prognosis for which no clinically approved antibodies exist. We found SCLC cell lines and primary samples expressed high levels of CD47 on their surface. Using human macrophages, we found that CD47-blocking therapies were able to induce macrophage phagocytosis of SCLC cells. Treatment of mice bearing primary human SCLC tumors with CD47-blocking antibodies was able to inhibit tumor growth and significantly prolong survival. To identify novel SCLC antigens that can be targeted in combination with high-affinity SIRPα variants, SCLC samples were screened by flow cytometry using comprehensive antibody arrays.

We validated tumor-specific antigens on the surface of SCLC cells, and identified antibodies to these antigens that could stimulate phagocytosis in vitro. When combined with high-affinity SIRPα monomers, the ability of these antibodies to stimulate phagocytosis was dramatically enhanced.

Example 2

CD47-Blocking Therapies Stimulate Macrophage Destruction of Small Cell Lung Cancer Small cell lung cancer (SCLC) is a highly aggressive subtype of lung cancer with dismal prognosis. There are no clinically approved antibodies, targeted therapies, or immunotherapies for the disease. We found that SCLC samples expressed high levels of CD47, a cell-surface molecule that allows cancer cells to evade the immune system. In particular, CD47 promotes immune evasion by signaling through SIRPα, an inhibitory receptor on macrophages. We hypothesized that CD47-blocking therapies could be applied to the treatment of SCLC. We found that CD47-blocking therapies were able to induce macrophage phagocytosis of SCLC samples in vitro. CD47-blocking therapies also inhibited tumor growth and significantly prolonged survival of mice bearing SCLC tumors. Furthermore, using comprehensive antibody arrays, we identified several new and established therapeutic targets on the surface of SCLC cells. Antibodies to these targets could elicit macrophage phagocytosis and were enhanced when combined with CD47-blocking therapies. These findings suggest that therapies that disrupt the CD47-SIRPα axis could benefit patients with SCLC, particularly when combined with tumor-specific antibodies.

Small cell lung cancer (SCLC), which derives from neuroendocrine cells of the lung, is one of the most lethal subtypes of cancer in humans. Each year, more than 25,000 patients are diagnosed with SCLC in the United States alone, and patients typically live only 6-12 months after diagnosis. The 5-year survival rate has remained dismal, hovering around 5% since the 1970s. Except for the combination of radiation and chemotherapy, there have been no new therapeutic approaches implemented in the past 30 years. Despite a plethora of clinical trials, no targeted therapies have been approved for SCLC. SCLC is strongly linked to heavy cigarette smoking, and increased smoking rates in developing countries will continue to increase the worldwide prevalence of SCLC in the future. For these reasons, there is a need to identify novel therapeutic targets and generate new treatments for patients with SCLC.

One of the most promising advances in the field of oncology is immunotherapy, which aims to stimulate a patient's own immune system to attack and eliminate cancer. As tumors develop, they acquire mechanisms to avoid destruction by the immune system. By understanding these mechanisms, we can develop new strategies to coax the immune system to recognize cancer as foreign. Previous studies have identified CD47, a cell-surface molecule, as a "marker of self" that prevents cells of the innate immune system from attacking hematologic malignancies and certain types of solid tumors. CD47 acts by sending inhibitory signals through SIRPα, a receptor expressed on the surface of macrophages and other myeloid cells. In this sense, the CD47-SIRPα interaction represents a myeloid-specific immune checkpoint. A number of reagents have been generated to disrupt signaling by the CD47-SIRPα axis, including anti-CD47 antibodies and engineered variants of its receptor, SIRPα. Recent studies have shown that blockade of CD47 lowers the threshold for macrophage phagocytosis of cancer. We hypothesized that SCLC cells also express CD47 and that CD47-blocking therapies could be used to stimulate macrophage phagocytosis of SCLC cells and inhibit growth of SCLC tumors in vivo.

Furthermore, CD47-blocking therapies have been shown to enhance the response of macrophages to monoclonal antibodies. Monoclonal antibodies—such as rituximab for lymphoma or trastuzumab for $Her^{2+}$ breast cancer—have demonstrated immense success for the treatment of cancer. No monoclonal antibodies are clinically approved for the treatment of SCLC, thus, we aimed to identify new SCLC surface antigens that could be targeted with monoclonal antibodies. While treatment with monoclonal antibodies can produce robust anti-tumor effects, they often fail to elicit cures when used as single agents, highlighting the need to improve the efficacy of these approaches. Therefore, we aimed to combine CD47-blocking therapies with other antibodies to achieve maximal anti-tumor responses against SCLC.

As a first step in our approach, we investigated whether CD47 was expressed on the surface of SCLC samples. Next, we examined whether CD47-blocking therapies could stimulate macrophage phagocytosis of SCLC in vitro. Mouse models of human cancer were used to evaluate the response of SCLC samples to CD47-blocking therapies in vivo. To identify new therapeutic targets on the surface of SCLC samples, we performed high-throughput flow cytometry using comprehensive antibody arrays. Last, we aimed to demonstrate that antibodies towards the identified antigens could be combined with CD47-blocking therapies to further increase phagocytosis. The overall objectives of this study were to validate CD47-blocking therapies for SCLC and identify additional antibodies that could be used to target SCLC. In this manner, we aim to identify new immunotherapeutic combinations that could be used for the benefit of patients with SCLC.

Results

Figure 5:
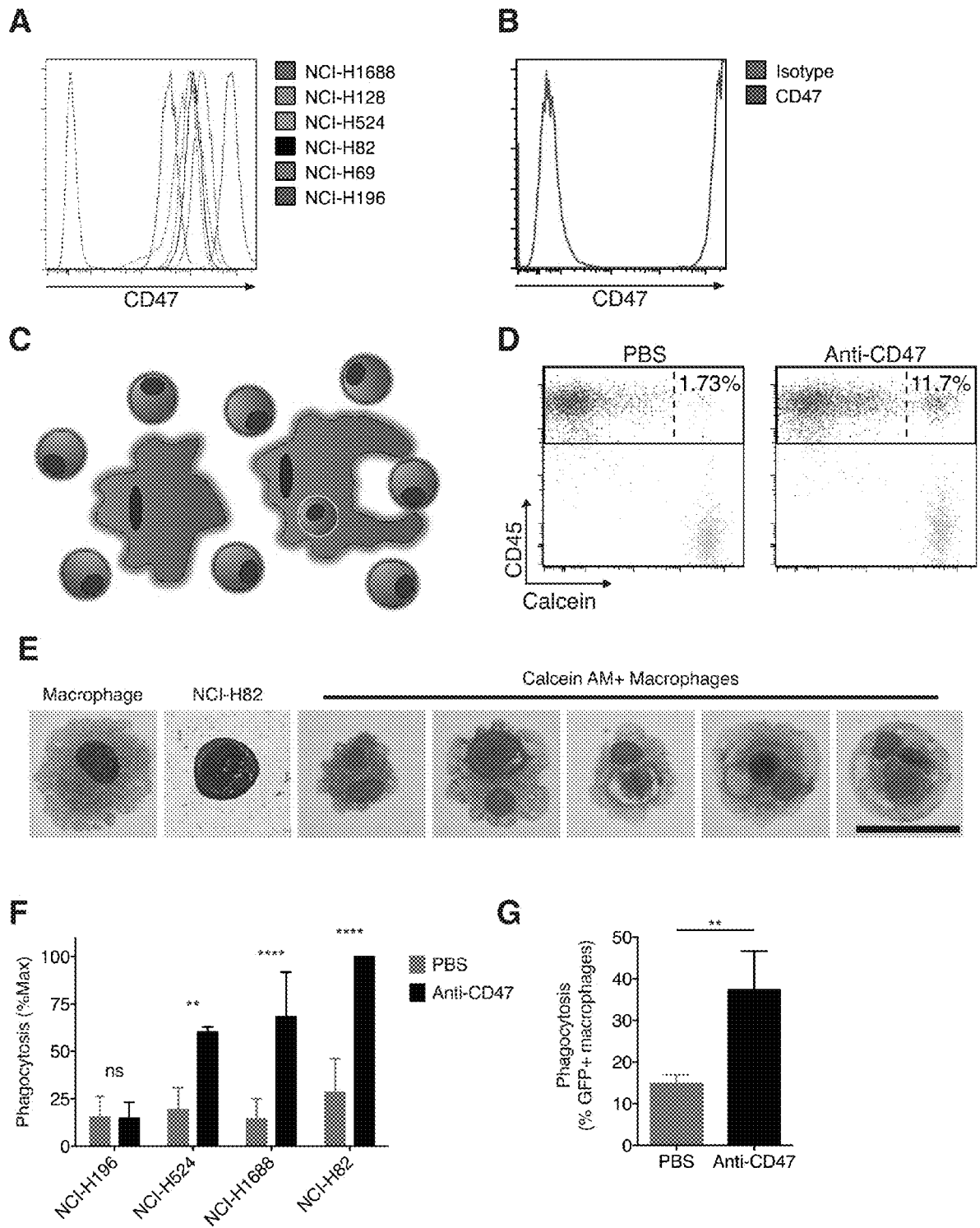
FIG. 5. CD47-blockade induces macrophage phagocytosis of SCLC cells in vitro. (A) Expression of CD47 on the surface of a panel of human SCLC cell lines as evaluated by flow cytometry. Black dotted line represents unstained NCI-H82 cells. (B) Expression of CD47 on the surface of the primary human SCLC sample H29. (C) Diagram depicting in vitro phagocytosis assays using human macrophages and fluorescent tumor cells. (D) Representative flow cytometry plots of phagocytosis assays performed with human macrophages and calcein AM-labeled SCLC cells. (E) Representative images of cell populations after fluorescence activated cell sorting. The sorted double-positive population contained macrophages with engulfed tumor cells. Scale bar represents 20 μm. (F) Summary of phagocytosis assays using human macrophages and calcein AM-labeled SCLC cells as analyzed by flow cytometry. SCLC cells were treated with vehicle control (PBS) or anti-CD47 antibodies (clone Hu5F9-G4). The percentage of calcein AM+ macrophages was normalized to the maximal response by each macrophage donor. (G) Phagocytosis of primary H29 SCLC cells by human macrophages after treatment with vehicle control (PBS) or anti-CD47 antibodies (clone Hu5F9-G4). (F-G) Phagocytosis assays were performed with macrophages derived from four independent blood donors. Data represent mean±SD. ns, not significant; P<0.01; **P<0.0001 for the indicated comparisons by two-way analysis of variance with Sidak correction (F) or two-tailed t test (G).

CD47 is Expressed on the Surface of SCLC. To evaluate whether CD47-blocking therapies could be applied to SCLC, we first examined expression of CD47 on the surface of SCLC cells. We obtained six SCLC cell lines and subjected them to flow cytometry to evaluate CD47 expression on the cell surface. All six cell lines exhibited high CD47 expression (FIG. 5A). We also evaluated CD47 surface expression on a SCLC patient-derived xenograft obtained from a primary SCLC patient sample. Similar to the cell lines, the H29 patient sample also expressed high levels of CD47 on its surface (FIG. 5B). These findings suggested that CD47 is an immunotherapeutic target on SCLC.

CD47-blocking Antibodies Induce Phagocytosis of SCLC by Human Macrophages. To validate CD47 as a genuine therapeutic target on SCLC, we performed in vitro phagocytosis assays using human macrophages and SCLC samples. Macrophages were co-cultured with SCLC cells in the presence of a vehicle control or anti-CD47 antibodies. We tested anti-CD47 antibody clone Hu5F9-G4, a humanized anti-CD47 antibody that blocks the interaction between CD47 and SIRPα and is under investigation in a Phase I clinical trial for solid tumors (ClinicalTrials.gov identifier: NCT02216409). High-throughput flow cytometry was used to measure phagocytosis, which was evaluated by the percentage of macrophages engulfing calcein AM-labeled SCLC cells (FIGS. 5C and D). Fluorescence-activated cell sorting was used to confirm the double positive population contained macrophages with engulfed tumor cells (FIG. 5E). Four SCLC samples were subjected to evaluation in phagocytosis assays. Three cell lines (NCI-H524, NCI-1688, and NCI-H82) exhibited significant increases in phagocytosis when treated with the CD47-blocking antibody (FIG. 5F). One cell line, NCI-H196, appeared to be resistant to phagocytosis, suggesting additional mechanisms modify the susceptibility of this cell line to macrophage attack. The patient-derived xenograft H29 was also subjected to phagocytosis assays with human macrophages. Treatment of this sample with anti-CD47 antibodies also resulted in a significant increase in phagocytosis (FIG. 5G).

Figure 6:
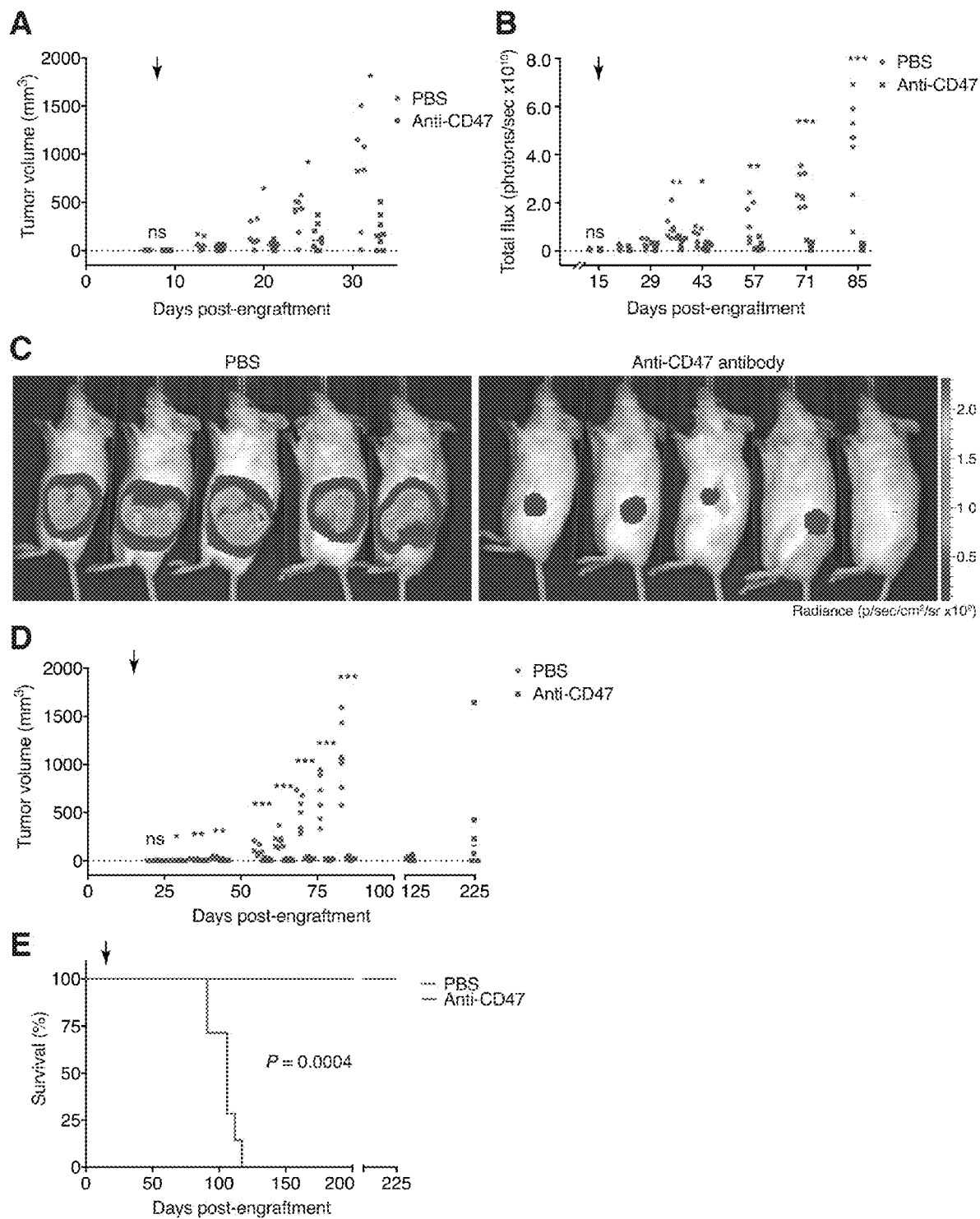
FIG. 6. CD47-blocking antibodies inhibit growth of human SCLC tumors in vivo. (A) Growth of NCI-H82 cells in the subcutaneously tissue of NSG mice. Mice were randomized into groups treated with vehicle control (PBS) or anti-CD47 antibodies (clone Hu5F9-G4). Growth was evaluated by tumor volume measurements. Seven to eight mice were treated per cohort, and each point represents tumor volume of independent animals. (B) Growth of GFP-luciferase+ patient-derived xenograft H29 tumors in the subcutaneous tissue of NSG mice as evaluated by bioluminescence imaging. Mice were randomized into groups treated with vehicle control (PBS) or anti-CD47 antibodies (clone Hu5F9-G4). (C) Representative bioluminescence images of H29 tumors on day 85 post-engraftment. (D) Growth of H29 tumors as evaluated by tumor volume measurements. (E) Survival of mice bearing patient-derived xenograft H29 tumors that were treated with the indicated therapies. P=0.0004 by Mantel-Cox test. A-E Black arrows indicate the start of treatment. Points indicate measurements from independent animals, bars indicate median values. Cohorts consisted of a minimum of 7-8 mice. Measurements at each time point are staggered for clarity. ns, not significant; *P<0.05; P<0.01; *P<0.001 for the indicated comparisons by Mann-Whitney test.

CD47-blocking Antibodies Inhibit Growth of SCLC Tumors in vivo. To evaluate the potential of CD47-blocking agents when administered as therapies for human SCLC, we established xenograft models of human SCLC. We engrafted NCI-H82 cells into the lower left flanks of NSG mice, which lack functional T cells, B cells, and NK cells but retain functional macrophages. Approximately one week after engraftment, mice were randomized into treatment with vehicle control or 250 μg anti-CD47 antibody clone Hu5F9-G4 administered every other day. Tumor volume measurements were used to evaluate mice for a response to therapy. After two weeks of treatment, a significant difference in median tumor volume was observed that persisted through the remainder of the experiment (FIG. 6A). After approximately one month of treatment, the median tumor volume for the vehicle control cohort was 837.8 mm$^3$ versus 160.2 mm$^3$ for the cohort treated with the anti-CD47 antibody (P=0.0281). Therefore, the CD47-blocking antibody was able to produce a significant inhibition of tumor growth.

We created a GFP-luciferase+NCI-H82 cell line to monitor growth and dissemination in vivo. As an orthotopic model of human SCLC, we engrafted GFP-luciferase+ NCI-H82 cells into the left intrathoracic space. Four days after injections, engraftment was confirmed by bioluminescence imaging. We then randomized mice into two cohorts treated with either vehicle control or 250 pg anti-CD47 antibody clone Hu5F9-G4 administered every other day. We monitored tumor growth over time by bioluminescence imaging. Again, the CD47-blocking antibody produced a significant inhibition of tumor growth. Additionally, we observed a significant benefit in survival for the cohort treated with the CD47-blocking antibody. Post-mortem analysis revealed tumors formed within the thoracic cavity or in the parathoracic region. Mice in the vehicle control group also exhibited substantial metastases to the liver, which were not observed in the cohort treated with the anti-CD47 antibody.

Since cell lines typically represent clonal populations of cells, we next tested the in vivo efficacy of CD47-blocking antibodies on a patient-derived xenograft, which more closely models treatment in patients since it maintains the heterogeneity of cancer cell populations within a tumor. Primary SCLC sample H29 was transduced to express GFP-luciferase to allow for dynamic measurements of tumor growth in vivo. Tumors were then engrafted into the lower left flanks of mice and allowed to establish for approximately 2 weeks. Mice were then randomized into two treatment cohorts with vehicle control or 250 μg anti-CD47 antibody clone Hu5F9-G4 administered every other day. We found the anti-CD47 antibody significantly inhibited tumor growth, as assessed by tumor volume measurements and bioluminescence imaging (FIG. 6B-D). Treatment with the CD47-blocking therapy also produced significant benefits in survival. By day 125 post-engraftment, all mice in the control group had died whereas the majority of mice in the anti-CD47 antibody group had only small tumors that failed to progress even after 225 days post-engraftment (FIG. 6E). These models demonstrate that CD47-blocking therapies could be effective for patients with SCLC.

Figure 7:
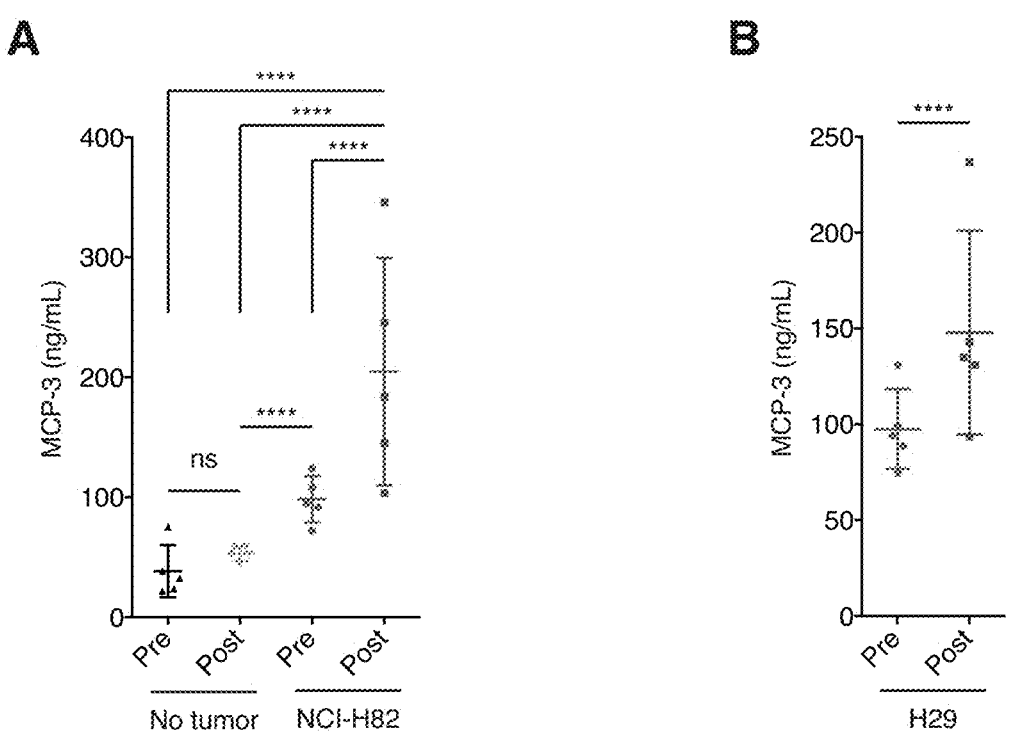
FIG. 7. MCP-3 is a serum biomarker that predicts response to CD47-blocking therapies. (A) Untreated NSG mice (No tumor) or NSG mice bearing subcutaneous NCI-H82 cells were injected with a single dose of anti-CD47 antibodies (clone Hu5F9-G4). Serum samples were collected pre-treatment or 24 hours post-treatment. MCP-3 levels were measured by Luminex multiplex array. (B) MCP-3 levels in mice bearing patient-derived xenograft H29 tumors were evaluated as in A. Points represent measurements from individual mice, bars represent mean±SD. Five mice were evaluated per condition. ns=not significant; ****P<0.0001 by two-way analysis of variance with Sidak correction.

Serum MCP-3 is a Biomarker of Response to CD47-blocking Therapies. To identify potential biomarkers of a response to CD47-blocking therapies, we again engrafted mice with NCI-H82 cells. We allowed tumors to grow to approximately 1.5 cm in diameter and then we treated the mice with a single dose of vehicle control or anti-CD47 antibody clone Hu5F9-G4. We collected serum samples immediately before treatment and 24 hours post-treatment. We subjected the serum samples to multiplex analysis of 38 cytokines. From this analysis, we found that macrophage chemotactic protein 3 (MCP-3) was systemically increased following treatment with anti-CD47 antibody clone Hu5F9-G4 (FIG. 7A). No significant increase in MCP-3 was observed in mice without tumors that were treated with anti-CD47 antibody clone Hu5F9-G4 (FIG. 7A). We also performed a similar experiment using the patient-derived xenograft H29. Again, mice bearing tumors were subjected to a single dose of anti-CD47 antibody clone Hu5F9-G4. Serum cytokine analysis again revealed that MCP-3 was significantly increased following treatment with the CD47-blocking antibody (FIG. 7B). Therefore, MCP-3 may serve as a biomarker of response to CD47-blocking therapies in patients. Secretion of MCP-3 may be a positive feedback mechanism that recruits more macrophages to the tumor and could in part explain the robust effects of CD47-blocking therapies in vivo.

Figure 8:
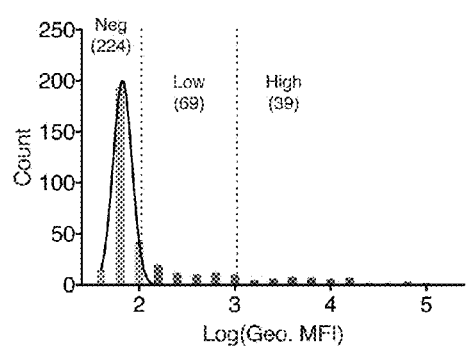
FIG. 8. Comprehensive FACS-based antibody screening identifies new and established therapeutic targets on SCLC. Antigen expression on the surface of four SCLC cell lines and primary patient sample H29 was assessed using LEGENDScreen Human Cell Screening Kits (BioLegend), a collection of 332 antibodies targeting cell surface antigens. Antibody binding was detected by fluorescence-activated cell sorting (FACS) analysis. (A) Histogram depicting geometric mean fluorescence intensity (MFI) of all antibodies screened for SCLC surface binding. Data represent median values for each antibody across all five SCLC samples. Data were fit to Gaussian distribution (black curve), and negative antigens (gray) were defined by median MFI less than two standard deviations above the mean. Low antigens (red) defined as MFI less than one order of magnitude above the negative threshold. High antigens (blue) defined as one order of magnitude greater than negative threshold. (B) Ranked list of the 39 antigens identified as 'high' based on median MFI across all five SCLC samples.
Figure 8:
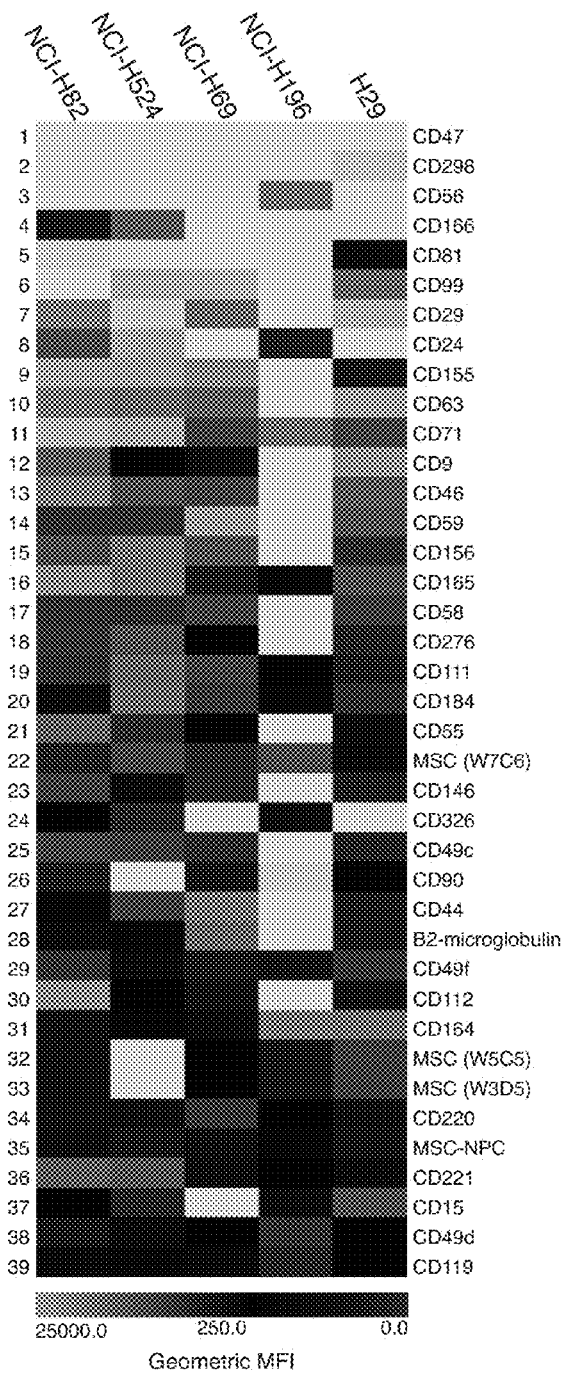

Comprehensive Antibody Arrays Identify Therapeutic Targets on SCLC. Monoclonal antibodies have proven to be some of the most effective treatments for cancer. However, there are few known antibody targets on the surface of SCLC. For this reason, we aimed to characterize the surface antigen profile of SCLC cells using comprehensive antibody arrays. We subjected four SCLC cell lines and the primary SCLC sample H29 to analysis using the BioLegend LEGENDScreen array, a comprehensive collection of 332 antibodies to human cell surface antigens. ***Discussion of histogram to define negative, low, and high antigens (FIG. 8A). We identified 39 antigens that were highly expressed on the surface of the SCLC samples, making them possible targets of therapeutic antibodies. When we ranked these antigens by their median staining intensity, we found that CD47 was the most intensely staining surface antigen (FIG. 8B). Another highly expressed antigen across all samples was CD56 (NCAM), a known marker of neuroendocrine tumors and a therapeutic target currently under evaluation for SCLC, thus validating our approach. A number of other highly expressed surface antigens were also identified that could potentially be targeted by monoclonal antibody therapies, including CD24, CD29, and CD99 (FIG. 8B). Interestingly, other immune checkpoint ligands such as CD80, CD86, PD-L1, or PD-L2 were not appreciably expressed on the surface of the SCLC samples.

Figure 9:
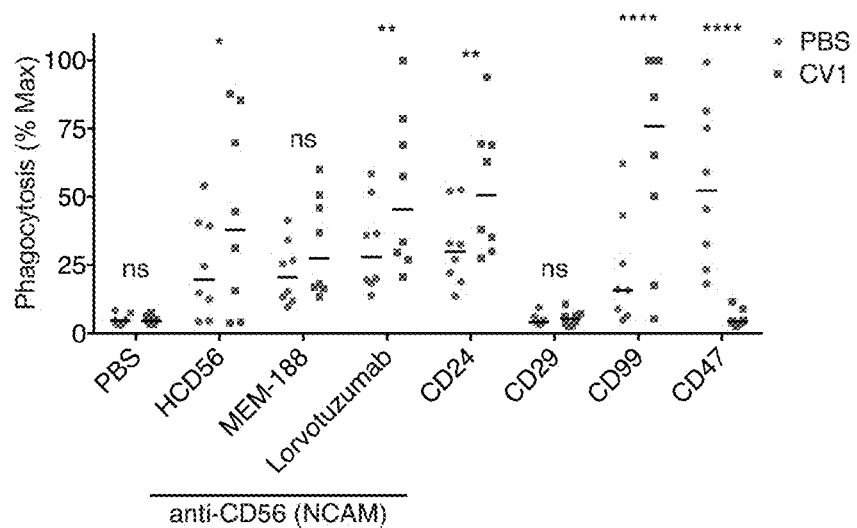
FIG. 9. High-affinity SIRPα variants enhance macrophage phagocytosis of SCLC in response to tumor-binding antibodies. Phagocytosis of NCI-H82 cells (A) and NCI-H524 cells (B) in response to tumor-binding antibodies alone (red) or in combination with the high-affinity SIRPα variant CV1 monomer (blue). Points represent measurements from individual donors, bars represent median values. Three clones of anti-CD56 (NCAM) antibodies were tested, as well as antibodies to CD24, CD29, CD99, and CD47 (clone Hu5F9-G4). (C) Phagocytosis of NCI-H82 SCLC cells in response to varying concentrations of the anti-CD56 antibody lorvotuzumab alone (red) or in combination with the high-affinity SIRPα variant CV1 monomer (blue). Data represent mean±SD. (A-C) Phagocytosis assays were performed with human macrophages derived from a minimum of four independent blood donors. Measurements were normalized to the maximal response by each macrophage donor. ns, not significant; *P<0.05; P<0.01; *P<0.001; ****P<0.0001 for the indicated comparisons by two-way analysis of variance with Sidak correction.
Figure 9:
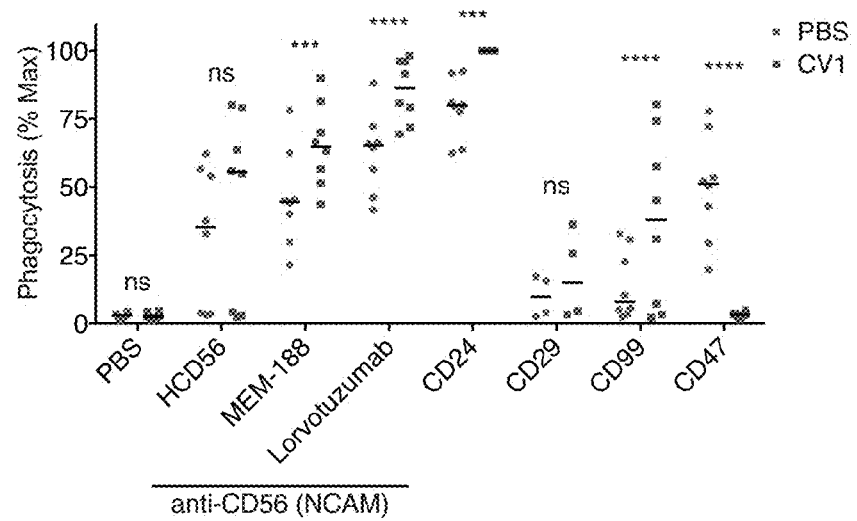
Figure 9:
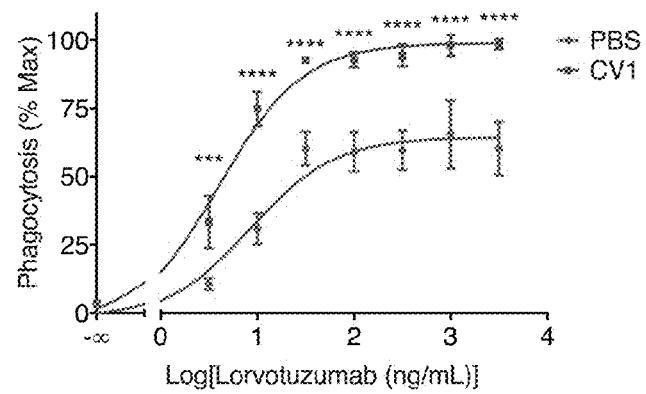

Combining Antibodies with CD47-blockade Enhances Phagocytosis of SCLC. To evaluate the therapeutic potential of the antigens identified by the LEGENDScreen arrays, we next evaluated their ability to be targeted by antibodies and induce phagocytosis in vitro. We obtained antibodies to a number of highly expressed surface antigens, including CD56 (clones HCD56 and MEM-188), CD24, CD29, and CD99. Additionally, we obtained the sequence for lorvotuzumab, an anti-CD56 antibody being evaluated in clinical trials as an antibody-drug conjugate, and we produced it recombinantly as a naked antibody. We tested these antibodies alone and in combination with the high-affinity CD47 antagonist CV1, which blocks CD47 but does not contribute an additional Fc stimulus (FIGS. 9A and B). We tested the ability of these antibodies to induce phagocytosis by human macrophages of two different SCLC cell lines, NCI-H82 (FIG. 9A) and NCI-H524 (FIG. 9B). Of the three anti-CD56 antibodies tested, we found that lorvotuzumab was able to produce the greatest increase in phagocytosis, and this effect was significantly enhanced by combination with CV1. Antibodies to CD24 or CD99 were also able to induce phagocytosis that was comparable or exceeded that of treatment with anti-CD47 clone Hu5F9-G4. As expected, phagocytosis with Hu5F9-G4 was entirely blocked when combined with CV1, since CV1 competes for the same binding surface and binds with extremely high affinity. Interestingly, the anti-CD29 antibody was not able to induce phagocytosis even in combination with CV1, an important demonstration that additional factors such as surface binding geometry or the ability to engage Fc receptors may modify the response of macrophages to therapeutic antibodies.

Since lorvotuzumab is under evaluation as a therapeutic agent for SCLC, we investigated its ability to induce phagocytosis over a varying range of concentrations. Treatment with lorvotuzumab alone produced a dose-response relationship for inducing macrophage phagocytosis. Importantly, we found that over each lorvotuzumab concentration tested, the addition of CV1 produced a greater degree of phagocytosis (FIG. 9C). These findings demonstrate that CV1 could increase both the maximal efficacy and the potency of lorvotuzumab, as previously observed when CV1 was combined with rituximab, trastuzumab, and cetuximab.

Due to its poor prognosis and dearth of effective treatment options, there is an imminent need to identify novel treatments for SCLC. Immunotherapies are emerging as some of the most promising new therapies for cancer, and here we show that CD47, the myeloid-specific immune checkpoint, is a genuine immunotherapeutic target for SCLC. CD47 was highly expressed on the surface of all SCLC samples tested, and we found blocking CD47 enabled macrophage phagocytosis of SCLC samples in vitro. Using multiple xenograft models, the CD47-blocking antibody Hu5F9-G4 was able to inhibit tumor growth and prolong survival of mice bearing SCLC tumors. Importantly, we observed anti-tumor efficacy in a patient-derived xenograft model of SCLC, which maintains the complexity of the tumor-initiating cell population and thus serves as a more accurate model for treatment in humans. Additionally we identified MCP-3 as a serum biomarker that correlates with response to CD47-blocking therapies. Since the anti-CD47 antibody Hu5F9-G4 is under investigation in a Phase I clinical trial for human solid malignancies (ClinicalTrials.gov identifier: NCT02216409), our findings provide scientific justification for further evaluation of anti-CD47 antibodies in subsets of patients with SCLC.

Furthermore, using comprehensive antibody arrays, we identified several antigens on the surface of SCLC samples that could be targeted with monoclonal antibodies therapies. Using the high-affinity SIRPα variant CV1, a next-generation CD47 antagonist, we found that CD47-blockade augmented the efficacy of anti-tumor antibodies for SCLC, as has been demonstrated for other cancers. The combination of high-affinity SIRPα variants with independent tumor-binding antibodies provided an optimal strategy for targeting CD47 in SCLC. Blockade of CD47 on the surface of SCLC was not sufficient to induce macrophage phagocytosis, but instead it augmented macrophage phagocytosis when SCLC-binding antibodies are present. Antibodies to CD56, CD24, and CD99 proved to be effective at inducing phagocytosis of SCLC, particularly when combined with CV1.

Additionally, we found that CD47-blockade was able to enhance the efficacy of lorvotuzumab, an antibody proceeding through clinical trials for SCLC as an antibody-drug conjugate (ADC) with the cytotoxic agent mertansine. Combining therapeutic antibodies with CD47-blocking therapies represents an alternative method to enhance the efficacy of therapeutic antibodies. One benefit of CV1 over ADCs is that it can be combined with any antibody without further engineering. ADCs often rely on internalization to deliver their cytotoxic payload, and this dependency can limit efficacy and increase side effects. Since CD47 blockade stimulates macrophages to identify cells for removal, there may be an added layer of specificity conferred by cell-cell interactions than that achieved by ADCs. Nonetheless, it is likely that even lorvotuzumab-mertansine could benefit from combination with CV1 if the ability to engage Fc receptors is preserved.

Our approach to identifying novel SCLC surface antigens can be applied to other types of cancer, and in the future could be used to assemble oligoclonal cocktails of antibodies that could be used to simulate the natural humoral immune response against foreign pathogens or cells. These cocktails could be combined with CD47-blocking therapies and other immunotherapies to mount an effective immune response against SCLC cells. These studies show that SCLC is responsive to CD47-blocking therapies.

Materials and Methods

Cell lines and culture: NCI-H82, NCI-524, NCI-H69, and NCI-1688 were obtained from ATCC. Cells were cultured in RPMI-1640 supplemented with 10% fetal bovine serum (Hyclone), 1× Glutamax (Invitrogen), and 100 U/mL penicillin and 100 ug/mL streptomycin (Invitrogen). Cell lines were grown in suspension (NCI-H82, NCI-524, NCI-H69) and dissociated by gentle pipetting or brief incubation with 1× TrypLE (Invitrogen). NCI-1688 cells were grown in adherent monolayers and or removed by brief incubation with 1× TrypLE. Cell lines were cultured in humidified incubators at 37° C. with 5% carbon dioxide.

Human macrophage differentiation: Leukocyte reduction system chambers were obtained from anonymous blood donors at the Stanford Blood Center. Monocytes were purified on an AutoMACS (Miltenyi) using CD14+ microbeads or CD14+ whole blood microbeads (Miltenyi) according to the manufacturer's instructions. Purified CD14+ monocytes were plated on 15 cm tissue culture dishes at a density of 10 million monocytes per plate. Monocytes were differentiated to macrophages by culture in IMDM supplemented with 10% Human AB serum (Invitrogen), 1× GlutaMax (Invitrogen), and 100 U/mL penicillin and 100 ug/mL streptomycin for approximately 7-10 days.

In vitro phagocytosis assays: In vitro phagocytosis assays were performed as previously described. Briefly, SLCC cancer cells were removed from plates and washed with serum-free IMDM. GFP-luciferase+ cells or cells labeled with calcein AM (Invitrogen) were used as target cells. Macrophages were washed twice with HBSS, then incubated with 1× TrypLE for approximately 20 minutes in humidified incubators at 37° C. Macrophages were removed from plates using cell lifters (Corning), then washed twice with serum-free IMDM. Phagocytosis reactions were carried out using 50,000 macrophages and 100,000 tumor cells. Cells were co-cultured for two hours at 37° C. in the presence of antibody therapies. After co-culture, cells were washed with autoMACS Running Buffer (Miltenyi) and prepared for analysis by flow cytometry. Macrophages were stained using fluorophore-conjugated antibodies to CD45 (BioLegend) in the presence of 100 µg/mL mouse IgG (Lampire). Dead cells were excluded from the analysis by staining with DAPI (Sigma). Samples were analyzed by flow cytometry using a LSRFortessa (BD Biosciences) equipped with a high-throughput sampler. Phagocytosis was evaluated as the percentage of calcein-AM$^+$ macrophages using FlowJo v9.4.10 (Tree Star) and was normalized to the maximal response by each independent donor where indicated. Statistical significance was determined and data were fit to sigmoidal dose-response curves using Prism 5 (Graphpad).

Additional reagents used in phagocytosis include the high-affinity SIRPα variant CV1 monomer, which was produced as previously described and used at a concentration of 1 µM for blocking. Antibodies to identified SCLC antigens were used in phagocytosis assays at a concentration of 10 µg/mL, including anti-CD56 (NCAM) clone HCD56 (BioLegend), anti-CD56 (NCAM) clone MEM-188 (BioLegend), anti-CD24 clone ML5 (Biolegend), anti-CD29 clone TS2/16 (BioLegend), anti-CD99 clone 12E7 (Abcam). Additionally, lorvotuzumab was made recombinantly using the heavy and light chain variable region sequences available in the KEGG database (Drug: D09927). Lorvotuzumab variable regions were cloned into pFUSE-CHIg-hG1 and pFUSE2-CLIg-hK (Invivogen) for expression. Lorvotuzumab was produced recombinantly by transient transfection of 293F cells (Invitrogen) using 293fectin (Invitrogen), followed by purification over a HiTrap Protein A column (GE Healthcare). Purified antibody was eluted with 100 mM citrate buffer (pH 3.0) and neutralized with $\frac{1}{10}^{th}$ volume of Tris buffer (pH 8.0). Antibody was desalted using a PD-10 column (GE Healthcare).

Sorting of macrophage populations after phagocytosis: 2.5 million human macrophages were combined with 5 million GFP$^+$ NCI-H82 cells and 10 pg/mL anti-CD47 antibody (clone Hu5F9-G4) in serum-free medium and incubated for two hours. Macrophages were identified by staining with anti-CD45, and macrophages populations were sorted on a FACSAria II cell sorter (BD Biosciences). Cells from sorted populations were centrifuged onto microscope slides then stained with Modified Wright-Giemsa stain (Sigma-Aldrich) according to the manufacturer's instructions and imaged on a DM5500 B upright light microscope (Leica).

Mice: Nod.Cg-Prkdc$^{scid}$ IL2rg$^{tm1Wjl}$/SzJ (NSG) mice were used for all in vivo experiments. Mice were engrafted with tumors at approximately 6-10 weeks of age, and experiments were performed with age and sex-matched cohorts. Mice were maintained in a barrier facility under the care of the Stanford Veterinary Services Center and handled according to protocols approved by the Stanford University Administrative Panel on Laboratory Animal Care.

In vivo SCLC treatment models: $1.25 \times 10^6$ NCI-H82 cells were subcutaneously engrafted into the flanks of NSG mice. Tumors were allowed to grow for 8 days, then mice were randomized into treatment groups with PBS or 250 pg anti-CD47 antibody (clone Hu5F9-G4). Treatment was administered every other day by intraperitoneal injection. Tumor growth was monitored by tumor dimension measurements that were used to calculate tumor volumes according to the ellipsoid formula ($\pi/6 \times \text{length} \times \text{width}^2$). For a patient-derived xenograft model of SCLC, $3 \times 10^6$ GFP-luciferase$^+$ H29 cells were subcutaneously engrafted with 25% Matrigel (BD Biosciences) into the flanks of NSG mice. Tumors were allowed to grow for 15 days, then mice were randomized into treatment with into treatment groups with PBS or 250 µg anti-CD47 antibody (clone Hu5F9-G4). Treatment was administered every other day by intraperitoneal injection. Tumor growth was monitored by bioluminescence imaging and tumor volume measurements as described above. Statistical significance of tumor growth was determined by Mann-Whitney test. Survival was analyzed by Mantel-Cox test. Pilot in vivo experiments with H82 cells and H29 cells were performed with smaller cohorts of mice with similar results.

GFP-fluorescence from tumor nodules was visualized on an M205 FA fluorescent dissecting microscope (Leica) fitted with a DFC 500 camera (Leica).

Bioluminescence imaging: Mice bearing GFP-luciferase+ tumors were imaged as previously described. Briefly, anesthetized mice were injected with 200 µL D-luciferin (firefly) potassium salt (Biosynth) reconstituted at 16.67 mg/mL in sterile PBS. Bioluminescence imaging was performed using an IVIS Spectrum (Caliper Life Sciences) over 20 minutes to record maximal radiance. Peak total flux values were assessed from the anatomical region of interest using Living Image 4.0 (Caliper Life Sciences) and were used for analysis.

Comprehensive FACS-based antibody screening: Antigens on the surface of SCLC samples were analyzed using LEGENDScreen Human Cell Screening Kits (BioLegend), according to the manufacturer's protocol with the following modifications. Briefly, lyophilized antibodies were reconstituted in molecular biology grade water and added to cell samples at a 1:8 dilution. Approximately 20-40×10$^6$ total cells were used for the analysis per SCLC sample. NCI-H82 was labeled with calcein-AM and analyzed simultaneously with NCI-H524. NCI-H69 was labeled with calcein-AM and analyzed simultaneously with NCI-H1688. The primary patient sample H69 was analyzed independently. It was freshly dissociated from a low-passage xenograft and mouse lineage cells were excluded from the analysis by staining with Pacific Blue anti-mouse H-2k$^d$ (BioLegend). Samples were incubated with antibodies for 30 minutes on ice protected from light. For all samples, dead cells were excluded from the analysis by staining with DAPI.

Jaiswal S, Jamieson C H, Pang W W, Park C Y, Chao M P, Majeti R, et al. CD47 is upregulated on circulating hematopoietic stem cells and leukemia cells to avoid phagocytosis. Cell. 2009; 138:271-85.

Majeti R, Chao M P, Alizadeh A A, Pang V W V, Jaiswal S, Gibbs K D, Jr., et al. CD47 is an adverse prognostic factor and therapeutic antibody target on human acute myeloid leukemia stem cells. Cell. 2009; 138:286-99.

Willingham S B, Volkmer J P, Gentles A J, Sahoo D, Dalerba P, Mitra S S, et al. The CD47-signal regulatory protein alpha (SIRPα) interaction is a therapeutic target for human solid tumors. Proceedings of the National Academy of Sciences of the United States of America. 2012; 109:6662-7.

Weiskopf K, Ring A M, Ho C C, Volkmer J P, Levin A M, Volkmer A K, et al. Engineered SIRPalpha Variants as Immunotherapeutic Adjuvants to Anticancer Antibodies. Science. 2013.

Chao M P, Alizadeh A A, Tang C, Myklebust J H, Varghese B, Gill S, et al. Anti-CD47 antibody synergizes with rituximab to promote phagocytosis and eradicate non-Hodgkin lymphoma. Cell. 142:699-713.

Maloney D G, Grillo-Lopez A J, White C A, Bodkin D, Schilder R J, Neidhart J A, et al. IDEC-C2B8 (Rituximab) anti-CD20 monoclonal antibody therapy in patients with relapsed low-grade non-Hodgkin's lymphoma. Blood. 1997; 90:2188-95.

Vogel C L, Cobleigh M A, Tripathy D, Gutheil J C, Harris L N, Fehrenbacher L, et al. Efficacy and safety of trastuzumab as a single agent in first-line treatment of HER2-overexpressing metastatic breast cancer. J Clin Oncol. 2002; 20:719-26.

Van Cutsem E, Kohne C H, Hitre E, Zaluski J, Chang Chien C R, Makhson A, et al. Cetuximab and chemotherapy as initial treatment for metastatic colorectal cancer. N Engl J Med. 2009; 360:1408-17.

Willingham S B, Volkmer J P, Gentles A J, Sahoo D, Dalerba P, Mitra S S, et al. The CD47-signal regulatory protein alpha (SIRPα) interaction is a therapeutic target for human solid tumors. Proc Natl Acad Sci USA.109:6662-7.

Shultz L D, Lyons B L, Burzenski L M, Gott B, Chen X, Chaleff S, et al. Human lymphoid and myeloid cell development in NOD/LtSz-scid IL2R gamma null mice engrafted with mobilized human hemopoietic stem cells. Journal of immunology. 2005; 174:6477-89.

What is claimed is:

1. A method of treating an individual with small cell lung cancer, the method comprising:
    administering to a human subject in need thereof a combination of (i) an antibody that binds to CD47 comprising a variable heavy (VH) region containing the VH complementarity regions, CDR1, CDR2 and CDR3, respectively set forth in SEQ ID NO:1, 2 and 3; and a variable light (VL) region containing the VL complementary regions, CDR1, CDR2 and CDR3, respectively set forth in in SEQ ID NO:4, 5 and, and (ii) an antibody free of drug conjugates that specifically binds to CD56 on cell surface of lung cancer cells, in a dose effective to increase depletion of the lung cancer cells.

2. The method of claim 1, wherein the combination of antibodies is administered simultaneously.

3. The method of claim 1, wherein the combination of antibodies is administered sequentially.

4. The method of claim 1, wherein the combination of antibodies is administered in overlapping dosing regimens.

5. The method of claim 1, wherein the individual is a human.

6. The method of claim 1, wherein the combination of agents provides for a synergistic effect.

7. The method of claim 1, wherein the anti-CD47 antibody comprises an IgG4 Fc region.

* * * * *